(12) United States Patent
Schraga

(10) Patent No.: US 6,530,937 B1
(45) Date of Patent: Mar. 11, 2003

(54) ADJUSTABLE TIP FOR A LANCET DEVICE AND METHOD

(75) Inventor: Steven Schraga, Surfside, FL (US)

(73) Assignee: Stat Medical Devices, Inc., Miami, FL (US)

(*) Notice: Subject to any disclaimer, the term of this patent is extended or adjusted under 35 U.S.C. 154(b) by 0 days.

(21) Appl. No.: 09/493,675

(22) Filed: Jan. 28, 2000

(51) Int. Cl.⁷ ............................ A61B 17/32; A61B 17/34
(52) U.S. Cl. ............................................ 606/182; 606/185
(58) Field of Search .......................... 606/1, 181–185; 600/461, 583; 604/192, 198, 263

(56) References Cited

U.S. PATENT DOCUMENTS

| | | |
|---|---|---|
| 676,678 A | 6/1901 | Ellifrits |
| 1,135,465 A | 4/1915 | Pollock |
| 2,848,809 A | 8/1958 | Crowder |
| 3,589,213 A | 6/1971 | Gourley |
| 4,139,011 A | 2/1979 | Benoit et al. |
| 4,257,561 A | 3/1981 | McKinney |
| 4,388,925 A | 6/1983 | Burns |
| 4,426,105 A | 1/1984 | Plaquin et al. |
| 4,449,529 A | 5/1984 | Burns et al. |
| 4,469,110 A | 9/1984 | Slama |
| 4,517,978 A | 5/1985 | Levin et al. |
| 4,785,858 A | 11/1988 | Valentini et al. |
| RE32,922 E | 5/1989 | Levin et al. |
| 4,834,667 A | 5/1989 | Fowler et al. |
| 4,858,607 A | 8/1989 | Jordan et al. |
| 4,895,147 A * | 1/1990 | Bodicky et al. |
| 4,924,879 A | 5/1990 | O'Brien |
| 4,976,724 A | 12/1990 | Nieto et al. |
| 5,147,375 A | 9/1992 | Sullivan et al. |
| 5,269,799 A | 12/1993 | Daniel |
| 5,304,193 A | 4/1994 | Zhadanov |
| 5,318,584 A | 6/1994 | Lange et al. |
| 5,324,303 A | 6/1994 | Strong et al. |
| 5,454,828 A | 10/1995 | Schraga |
| 5,464,418 A | 11/1995 | Schraga |
| 5,509,345 A | 4/1996 | Cyktick |
| 5,554,166 A | 9/1996 | Lange et al. |
| 5,569,287 A | 10/1996 | Tezuka et al. |
| 5,613,978 A * | 3/1997 | Harding .............. 606/181 |
| 5,628,764 A | 5/1997 | Schraga |
| 5,628,765 A | 5/1997 | Morita |
| 5,730,753 A | 3/1998 | Morita |
| 5,797,942 A | 8/1998 | Schraga |
| 5,873,887 A | 2/1999 | King et al. |
| 5,908,434 A | 6/1999 | Schraga |
| 5,916,230 A * | 6/1999 | Brenneman et al. ...... 606/182 |
| 5,984,940 A | 11/1999 | Davis et al. |
| 6,022,366 A | 2/2000 | Schraga |
| 6,045,567 A | 4/2000 | Taylor et al. |
| 6,056,765 A * | 5/2000 | Bajaj et al. .............. 606/182 |
| D428,150 S | 7/2000 | Ruf et al. |

FOREIGN PATENT DOCUMENTS

| | | |
|---|---|---|
| CA | 523078 | 3/1956 |
| FR | 1126718 | 11/1956 |

OTHER PUBLICATIONS

Sutor et al., "Bleeding form Standardized Skin Punctures: Automated Technic for Recording Time, Intensity, and Pattern of Bleeding", *A.J.C.P.*, vol. 55, pp. 541–549 (May 1971).

\* cited by examiner

*Primary Examiner*—Angela D. Sykes
*Assistant Examiner*—P. M. Bianco
(74) *Attorney, Agent, or Firm*—Greenblum & Bernstein, P.L.C.

(57) ABSTRACT

A lancet device, a tip for a lancet device and method of using the lancet device. The lancet device has a body portion for firing the lancet and a tip portion. The tip for a lancet device includes a front assembly which includes a side wall portion, a skin-engaging portion at least partially defining a plane beyond which a lancet needle may extend, and a lancet stop element, a slot is disposed in one of the sidewall portion and the lancet stop element, and at least one following element extending into the slot, wherein the lancet stop element is moveable towards and away from the plane in response to movement of the at least one following element. The method includes adjusting a set depth of penetration of the needle by moving the at least one following element, disposing the distal end of the lancet device against a surface of skin, and triggering the firing mechanism to cause the needle to penetrate the surface of the skin to the set depth, wherein the puncture allows a blood sample to be taken.

75 Claims, 25 Drawing Sheets

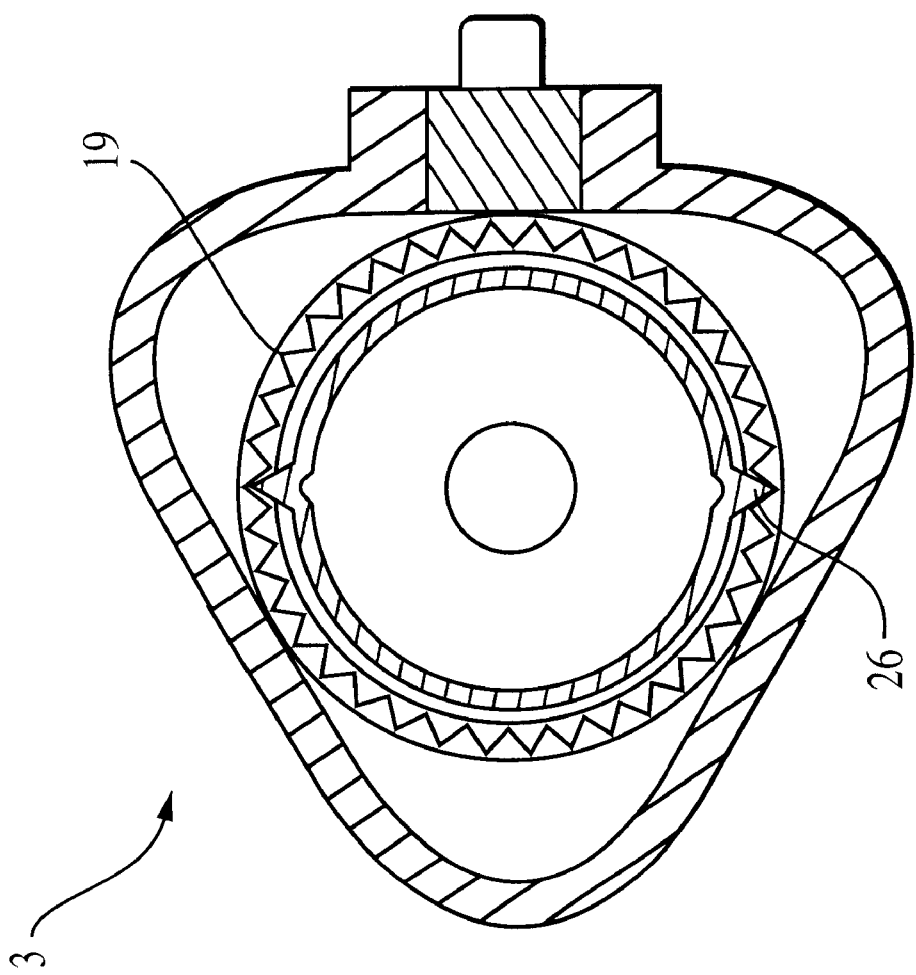

ADJUSTABLE TIP FOR A LANCET DEVICE AND METHOD

BACKGROUND OF THE INVENTION

1. Field of the Invention

The invention relates to a lancet device, an adjusting front mechanism for use on a lancet device, and a method of using a lancet device, In particular, the invention includes a lancet device which utilizes an adjustable tip or front. Lancet devices are used to penetrate and puncture the skin in order to allow the taking of a blood sample for testing. The device allows the user to control the depth of this penetration by a simple adjustment mechanism.

2. Discussion of Background Information

Lancet devices are commonly used to prick the skin of the user so that one or more drops of blood may be extracted for testing. Some users such as diabetics, for example, may have to test their blood sugar levels several times a day. This may be accomplished by the user using a simple needle. However, this procedure is often problematic for the user since the needle may be difficult to handle. Moreover, controlling the depth of penetration cannot be reliably accomplished without the use of a mechanical device. Additionally, many users simply cannot perform the procedure owing to either a fear of needles or because they lack a steady hand. As a result, lancet devices have been developed which allow the user to more easily and reliably perform this procedure.

Presently, most lancet devices lack convenient and flexible adjustability. Such devices are typically made adjustable by switching their tips. U.S. Pat. No. Re. 32,922 to LEVIN et al. is one such device. That is, the user must remove one tip having a set depth and replace it with another having a different set depth. This, of course, creates the problem of storing the replaceable tips, which if not properly done, may result in their misplacement, damage, contamination, or the like.

An improved device would allow the user to more easily adjust the depth of penetration and would overcome some of the disadvantages described above. Moreover, since the skin thickness can vary slightly from user to user and finger to finger, a need exists for efficiently adapting the depth of penetration. For example, an index finger may be more calloused than a middle finger, and the more calloused finger will typically have a thicker skin. By adjusting the depth of puncture so that the depth is no greater than necessary for extracting a required amount of blood, any pain experienced by the user may be minimized.

Lancets having an adjustable tip are known per se. For example, U.S. Pat. No. 4,469,110 to SLAMA discloses a mechanism which adjusts the penetration depth by rotating a threaded sleeve relative to a body. The SLAMA device is characterized as a "single bottom" device which employs a threaded design which can be expensive to manufacture. Moreover, such a device may require the user to rotate the threaded sleeve up to 360 degrees and more in order to attain the proper depth setting. Further, such a threaded resign is prone to inadvertent setting changes since there is nothing but frictional engagement between the mating threads to maintain the adjustment setting.

U.S. Pat. No. 4,895,147 to BODICKY et al. functions in a similar manner to the device in SLAMA and therefore suffers from similar disadvantages.

U.S. Pat. Nos. 5,464,418 and 5,797,942 and 5,908,434 to SCHRAGA also disclose similar lancet devices and are hereby incorporated herein by reference as though set forth in full herein.

As disclosed in U.S. Pat. No. 5,908,434, the lancet device has a body portion which encloses a lancet and a lancet firing mechanism. The lancet typically has a needle extending therefrom and is caused to move towards the tip of the device by a trigger or firing mechanism. The lancet device forces the needle, by virtue of the needle being fixed thereto, out of the device by some distance or depth so that the needle can penetrate the skin of the user. The function of this firing mechanism and the lancet body design is disclosed in each of U.S. Pat. Nos. 5,797,942 and 5,908,434. These Patents are incorporated by reference herein in their entirety and are therefore only briefly discussed herein.

What is needed is a front cap or tip design which can accurately and precisely control the depth of penetration of the needle relative to the surface of the user's skin. The front cap forms the tip portion of the lancet device. It uses an adjustment sleeve which resembles a nut and which is rotatable by the user. The nut has circumferential grooves and projections which help the user to grip it with his fingers. The nut is rotatable with respect to the front cap and/or the lancet body. Located on the inside the front cap is disposed a stop cap which is moveable in at least two directions. The stop cap can move forwards and backwards in the direction of the movement of the lancet and needle. Moreover, the stop cap can also rotate.

Thus, while advances have been made, there is a continuing need for a lancet device which provides for convenient and reliable adjustment of penetration depth.

SUMMARY OF THE INVENTION

According to one aspect of the invention there is provided a tip for a lancet device, which includes a front assembly comprising a side wall portion, a skin-engaging portion at least partially defining a plane beyond which a lancet needle may extend, and a lancet stop element, a slot disposed in one of the sidewall portion and the lancet stop element, and at least one following element extending into the slot, wherein the lancet stop element is moveable towards and away from the plane in response to movement of the at least one following element. The tip may include at least one actuator for engaging the at least one following element. The actuator may be a rotatable annular member for engaging the at least one following element. The at least one following element may be fixed to the stop member. Alternatively, the at least one following element may be fixed to the annular member. The slot may be disposed on the sidewall portion. The slot may be a camming slot. The slot may be both disposed on the stop member and may be a camming slot.

The tip may also include an outer generally annular rotatable member. The at least one following element may be fixed to the generally annular rotatable member. The generally annular rotatable member may have a slot. The slot on the generally annular rotatable member may be a camming slot. The at least one following element may be fixed to the stop member.

The tip may include at least one tooth disposed on one of the stop member and the front assembly. The front assembly may include an internal spline having a plurality of teeth for engaging the at least one tooth disposed on the stop member. The tip may have at least two ratchet teeth being disposed on the stop member approximately 180 degrees apart from one another. The stop member may include a first section which includes at least one ratchet tooth and a second section which includes a camming lug, the first section being partially separated from the second section by at least one separating slot. The first section and the second section may be partially separated by at least two separating slots such that the separating slots define at least two connecting walls. The second section may further include a deflecting wall for connecting the camming lug to a cylindrical wall of the stop cap. The second section may include a circumferential separating slot for separating a portion of the deflecting wall from the cylindrical wall of the stop member such that the deflecting wall is connected to the cylindrical wall by a connecting wall. The connecting wall allows the deflecting wall to deflect inward towards a center axis of the stop member. The stop member may be moveably retained within the front assembly such that it can rotate and move axially with respect to the front assembly. The stop member may be moveable towards and away from the plane such that at least one ratchet tooth maintains engagement with an internal spline disposed on an internal surface of the front assembly throughout this movement.

The tip may provide that the at least one following element is guided within the slot when the stop member is moved axially or rotated. The front assembly may include a bearing surface disposed between at least two shoulders, and wherein an annular member is rotatably disposed on the bearing surface and is retained from axial movement by at least one shoulder. The front assembly may further include engaging lugs which cooperate with engaging grooves on a lancet body and a manual lancet release button for separating the lancet from the lancet body. The lancet stop element may include a opening for allowing the needle to project therethrough.

The tip may further include a rotatable nut disposed on the front assembly which includes one of a plurality of projections and grooves disposed on an outer surface. The nut may include indicating marks and the front cap may further comprise a reference mark. The nut may also include a distal wall which includes an opening for allowing the needle to project therethrough.

According to still another aspect of the invention, there is provided a lancet device, which includes a lancet body including a lancet firing mechanism which is at least partially enclosed within a lancet body shell, a front assembly including a side wall portion, a skin-engaging portion at least partially defining a plane beyond which a lancet needle may extend, and a lancet stop element, a slot disposed in one of the sidewall portion, the lancet stop element, and the outer generally annular member, and at least one following element extending into the slot, wherein the lancet stop element is moveable towards and away from the plane in response to movement of the at least one following element.

The invention also provides for a front cap mechanism for a lancet device wherein the front cap mechanism includes a proximal end for attaching to the lancet device and a distal end for allowing a needle to project therefrom, the lancet having a surface from which the needle projects, the mechanism including a front cap having a distal opening adapted to allow the needle to project therethrough, a nut rotatably disposed on an outer surface of the front cap, a stop cap disposed within the front cap and adapted to allow the needle to project therethrough, the stop cap including a lancet stop surface and an opening, wherein the lancet stop surface is adapted to allow the needle to project through the opening and is adapted to prevent further movement of the lancet when the lancet surface contacts the lancet stop surface.

The mechanism may provide that the stop cap further includes at least one ratchet tooth and wherein the front cap further comprises an internal spline having a plurality of teeth for engaging the at least one ratchet tooth. The at least one ratchet tooth may be at least two ratchet teeth disposed approximately 180 degrees apart from one another. The stop cap may include a first section which includes at least one ratchet tooth and a second section which includes at least one camming lug, the first section being partially separated from the section by at least one separating slot. The first section and the section may be partially separated by at least two separating slots such that the separating slots define at least two connecting walls. The second section may include a deflecting wall for connecting the camming lug to a cylindrical wall of the stop cap. The camming lug may be guided within the circumferential camming slot when the stop cap is moved axially or rotated and wherein the camming lug engages a recess formed on the nut. The second section may also include a circumferential separating slot for separating a portion of the deflecting wall from the cylindrical wall of the stop cap such that the deflecting wall is connected to the cylindrical wall by a connecting wall. The stop cap may be moveably retained within the front cap such that it can rotate and move axially with respect to the front cap. The rotation of the nut in one direction may cause movement of the lancet stop surface towards the distal end and wherein rotation of the nut in the opposite direction may cause movement of the lancet stop surface away from the distal end.

According to another aspect of the invention, there is provided a method of puncturing a surface of skin using a lancet device which includes a lancet firing mechanism and a tip for a lancet device comprising a front assembly comprising a side wall portion, a skin-engaging portion at least partially defining a plane beyond which a lancet needle may extend, and a lancet stop element, a slot disposed in one of the sidewall portion and the lancet stop element, and at least one following element extending into the slot, wherein the lancet stop element is moveable towards and away from the plane in response to movement of the at least one following element, the method comprising adjusting a set depth of penetration of the needle by moving the at least one following element to a set position, disposing the distal end of the lancet device against a surface of skin, and triggering the firing mechanism to cause the needle to penetrate the surface of the skin to the set depth, wherein the puncture allows a sample of blood to be taken. The sample may comprise at least one drop of blood which flows up to the surface of the skin.

The invention also provides for a method of puncturing a surface of skin using a lancet device comprising a lancet body comprising a lancet firing mechanism which is at least partially enclosed within a lancet body shell, a front assembly comprising a side wall portion, a skin-engaging portion at least partially defining a plane beyond which a lancet needle may extend, and a lancet stop element, a slot disposed in one of the sidewall portion, the lancet stop element, and the outer generally annular member, and at least one following clement extending into the slot, wherein the lancet stop element is moveable towards and away from the plane in response to movement of the at least one following element, the method comprising adjusting a set depth of penetration of the needle by moving the at least one following element to a set position, disposing the distal end of the lancet device against a surface of skin, and triggering the firing mechanism to cause the needle to penetrate the surface of the skin to the set depth, wherein the puncture allows a blood sample to be taken. The sample may comprise at least one drop of blood which flows up to the surface of the skin.

The invention therefore provides for a lancet device and a method of using the device to extract one or more drops of blood for testing. The invention also provides a front mechanism which may be in the form of a cap and which is adaptable to be used on conventional lancet devices for facilitating precise needle depth control. Moreover, the invention provides such a device which may be a hand held device which is small enough to be placed in a pocket or purse. It has a body portion and a front cap or tip portion and functions in a manner similar to the devices disclosed in U.S. Pat. No. 5,908,434 and U.S. Pat. No. 5,797,942, each issued to SCHRAGA, the disclosure of each being incorporated by reference herein in their entirety. Both these Patents were issued to this inventor.

The invention provides for a front mechanism having an adjustment mechanism. This front mechanism may be utilized on many conventional lancet devices, and in particular, may be used on the above listed devices. Further, the invention provides for a new type of lancet which utilizes this adjustment front cap mechanism. In one embodiment, the front assembly or front mechanism is in the form of a cap.

The stop cap also has a camming lug which travels in a camming slot formed in a side wall of the front cap. The lug projects through the camming slot and further into a recess formed on an inside surface of the nut. In operation, this design allows the stop cap to rotate as well as move forwards and backwards, based upon rotational movement of the nut. The camming slot in the front cap is angled in such a way to allow the stop cap to be precisely positioned within the front cap. The stop cap functions, as its name suggests, as a stop for the lancet. That is, it acts to stop the movement of the lancet after it is fired in the direction of the tip. For this purpose, the stop cap has a stop surface which prevents the lancet from moving any further past a set point. Moreover, the stop cap includes a through hole which allows the needle to protrude therethrough. As a result of the needle being fixed to the lancet, the stop cap also prevents the needle's movement past a set point.

The device functions as follows: a user rotates the nut in either a clockwise or counterclockwise direction to set or adjust the device to a certain set needle depth. This is facilitated by indicating marks formed on the nut with respect to a reference mark formed on the from cap in the form of a reference arrow. The rotation of the nut causes movement of the stop cap to a set position for prevention further movement of the lancet and needle. At this point, the user places the device with the front cap positioned against the skin. Upon activation of the trigger mechanism, the lancet and needle are caused to move towards the skin. However, the lancet and needle will not be allowed to travel past a stop point determined by the stop cap. As a result, the needle protrudes into the skin only by the desired maximum amount. That is the needle can penetrate only up to the point where the lancet contacts the stop surface. The needle penetrates and is retracted very quickly owing the speed of the spring activated plunger and firing mechanism which causes the lancet to move. At this point the user withdraws the device from the skin and stores it for later use. A drop of blood should then flow up through the puncture in the skin which can be tested.

However, should an insufficient amount of blood not surface from the puncture, the device can be re-adjusted to allow the needle to penetrate still a little further into the skin. To do so, the user merely rotates the nut in the required direction to the next indicating mark. This will in turn, cause the stop cap to move closer toward the user's skin. The lancet device can then be rearmed and triggered, and once released will allow the needle to penetrate a little further into the skin. Of course, if an excessive amount of blood flows up or if an excessive amount of pain is experienced owing to the needle penetrating too much, then the nut can be rotated in the opposite direction to reduce the depth of needle penetration.

In one particular embodiment of the device, the nut is located on the front cap and sits back some distance from a distal surface. The distal surface being a surface which contacts the skin of the user and through which the needle projects. One advantage of this embodiment is that the nut may be easier to fabricate.

In another embodiment of the device, the nut itself includes the distal surface with the corresponding distal opening. One advantage of this embodiment is that the nut has a longer axial length which can be easier to grip. Another advantage is that the front cap may be easier to fabricate owing to its cylindrical shape having both ends open.

The invention thus provides for a front cap adjusting mechanism which can be adapted to fit on conventional lancet devices for facilitating precise needle penetration. Moreover, the invention provides for a lancet which uses the front cap. Finally, the invention provides for a method of using the device to extract blood for testing.

As explained above in connection with the device, the method allows the user to extract one of more drops of blood more efficiently, precisely, consistently, and with less discomfort to the user.

Other exemplary embodiments and advantages of the present invention may be ascertained by reviewing the present disclosure and the accompanying drawing.

BRIEF DESCRIPTION OF THE DRAWINGS

The present invention is further described in the detailed description which follows, in reference to the noted plurality of drawings by way of non-limiting examples of exemplary embodiments of the present invention, in which like reference numerals represent similar parts throughout the several views of the drawings, and wherein:

FIG. 9, shows a greatly enlarged view of FIG. 7 in which the interaction between the stop cap ratchet teeth and the front cap internal spline are seen more clearly;

FIG. 32, shows the front cap mechanism of another embodiment in which the front cap has a longitudinal slot instead of the nut, this design can be used with any of the nuts shown in FIGS. 26–29 and would function with stop cap 25 or 25a.

DETAILED DESCRIPTION OF THE PRESENT INVENTION

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show structural details of the present invention in more detail than is necessary for the fundamental understanding of the present invention, the description taken with the drawings making apparent to those skilled in the art how the several forms of the present invention may be embodied in practice.

Figure 1:
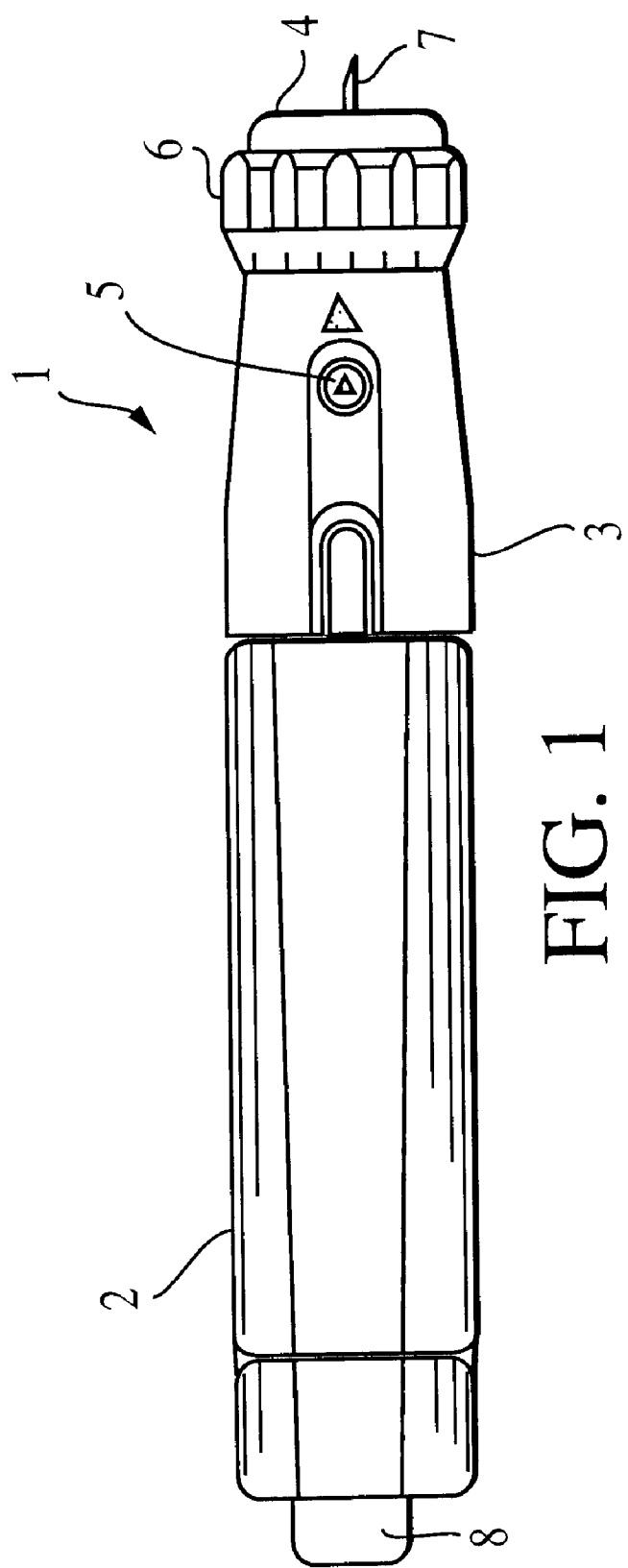
FIG. 1, shows a side view of one embodiment of the lancet device.

FIG. 1 shows one embodiment of lancet device 1. Lancet device 1 has a lancet body portion 2 and a front assembly or front cap mechanism 3 (also referenced herein as a tip or front portion). In one particular embodiment lancet device 1 includes a rear trigger mechanism 8 in the form of a push button. The details of this type of trigger mechanism or a similar type device may be found in, for example, U.S. Pat. Nos. 5,908,434 and/or 5,797,942, which are hereby incorporated by reference herein in their entirety for this purpose. Moreover, front cap mechanism 3 may include the feature of a manual release mechanism 5, as is fully described in U.S. Pat. No. 5,797,942. Front cap mechanism 3 is removably attached to lancet body 2 by separating engaging mechanisms of the two parts. For example, front cap 3 may have engaging lugs 22 (see FIG. 6) disposed on an inside engaging surface which snap into engaging grooves on an external surface of lancet body 2. The attachment may also be a simple overlapping sliding interference fit such as that disclosed in U.S. Pat. No. 5,464,418, which Patent is hereby incorporated by reference in its entirety for this purpose.

As can be seen in FIG. 1, lancet device 1 includes front assembly or front cap mechanism 3 having distal surface 4 which forms the contact surface which is pressed against the surface of the user's skin. A needle 7 is allowed to project past this surface for a set depth after the trigger is pushed. This distal surface 4 may comprise a skin-engaging portion defining a plane through which needle 7 may extend. Shortly after being triggered, needle 7 is retracted back into device 1. It should be noted that although FIG. 1 shows needle 7 in a projected state, the reality is that this extended state occurs only for a very short period of time, on the order of for example, a fraction of a second. The mechanism controlling the movement of lance 37 and needle 7, and its ability to retract back into device 1, is disclosed in the above noted Patents which have been incorporated by reference. Moreover, the invention contemplates that front cap mechanism 3 can be used with other lancet body types, provided a proper mating configuration is established.

Front cap mechanism 3 may have a skin engaging portion which at least partially defines a plane beyond which needle 7 may project. In the embodiment of FIG. 1, this skin engaging portion is defined by contact surface 4. However, the invention contemplates that this plane may also be defined by any number of structures, such as, two or more contact points or projections extending from either nut 6 or some distal portion of front cap 3. In this case, these structures would form the contact plane between lancet device 1 and a user's skin surface.

Figure 2:
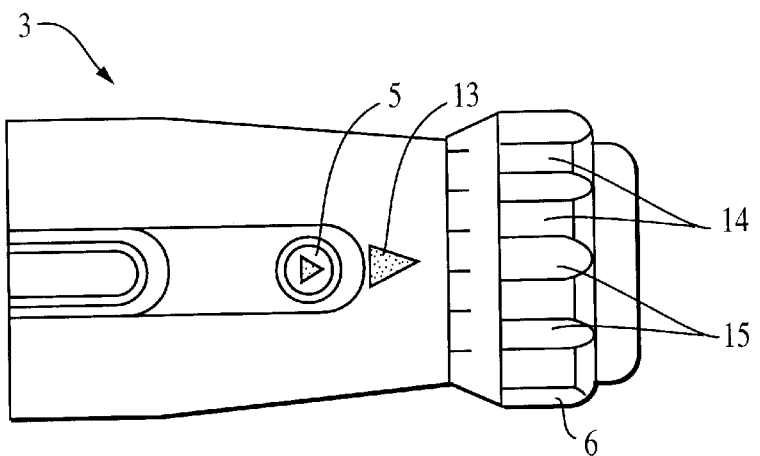
FIG. 2, shows a side view of the front cap mechanism of the embodiment of FIG. 1.

FIG. 2 shows an enlarged view of front cap mechanism 3 of the embodiment of FIG. 1. Front cap mechanism 3 includes manual release button 5 as previously discussed. A reference marker arrow 13 is also preferably provided and is preferably integrally formed with front cap 3. A generally annular member 6 (also referred to as an outer sleeve or nut) is disposed on front cap 3 and is allowed to rotate with respect to front cap 3. Annular member or nut 6 includes projections 14 and grooves 15 which may be formed integrally with nut 6. Projections 14 and grooves 15 allow nut 6 to be gripped more easily by the user. In particular, the user clamps nut 6 between his thumb and index finger, and then proceeds to rotate it. Nut 6 may be rotated clockwise or counter clockwise for some angle of rotation that should preferably be less than approximately 360 degrees and preferably around approximately 180 degrees.

Figure 3:
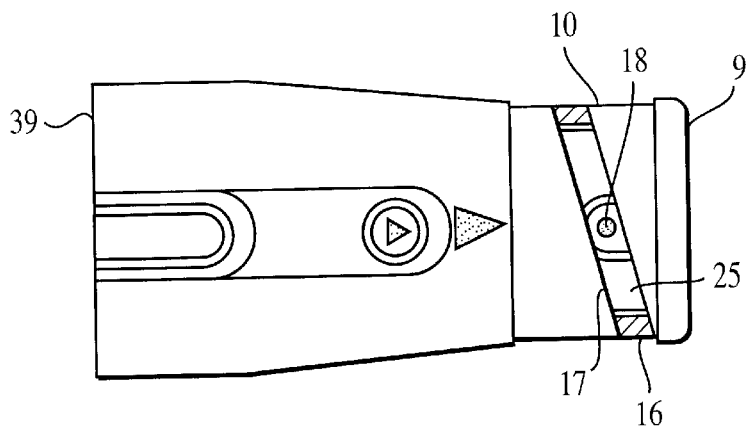
FIG. 3, shows the front cap mechanism of FIG. 2 with the nut removed therefrom.

FIG. 3 shows front cap mechanism 3 with nut 6 removed. Front cap 3 has a proximal end 39 which is adapted and/or configured to attach conveniently to lancet body 2, so as to form lancet device 1. Front cap 3 also has bearing surface 10 which represents a surface upon which nut 6 can rotate. As can be seen in FIG. 3, front cap 3 also has a slot 17 in the form of a camming slot (or a longitudinal slot in another embodiment, see for example FIG. 32) and which is a slot extending through a front cap side wall 16, Camming slot 17 acts as a guide for camming lug 18 of stop cap 25 member, which in this embodiment is in the form of a cap stop. Camming slot 17 should extend approximately halfway through or across the circumference of bearing surface 10 of front cap 3. This would provide for approximately 180 degrees of total rotational movement of nut 6. Nevertheless, greater or lesser ranges of rotational movement are also contemplated by the invention. Moreover, camming slot 17 may have many configurations, such as for example, having a serpentine or snake shape which would facilitate greater degrees of depth adjustment.

Figure 4:
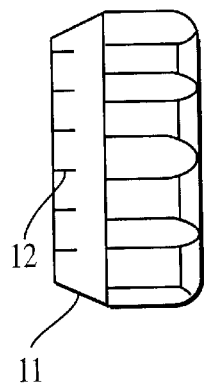
FIG. 4, shows a side view of the nut shown in FIG. 2 by itself.

FIG. 4 shows nut 6 removed from front cap 3. Nut 6 also has indicating marks 12 which may be in the form of numbers or letters (not shown) or simply lines. Indicating marks 12 represent specific needle depth settings. The device 1 may further utilize a zero setting, which can represent a typical skin depth and include positive and negative values disposed on either side, to designate greater and lesser depth penetrations. Alternatively, indicating marks 12 may indicate a range of letters or numbers (not shown) designating from lesser to greater, the depth of penetration values. For example, an "A" setting may represent one depth penetration with the next mark adjacent mark being a "B" setting and representing a slightly greater depth penetration. Moreover, the particular configuration of nut 6 is important only with respect to its ability to move the stop cap or member 25 to a desired position. As such, the nut may alternatively utilize indicating marks 12 and/or tapered section 11 on the distal side of nut 6. In such a design, arrow 13 could be located in a position on the side wall between the distal end of nut 6, once installed, and distal end 9 of front assembly (not shown). Alternatively, nut 6 may include an arrow 13 while front assembly has indicating marks 12.

Figure 5:
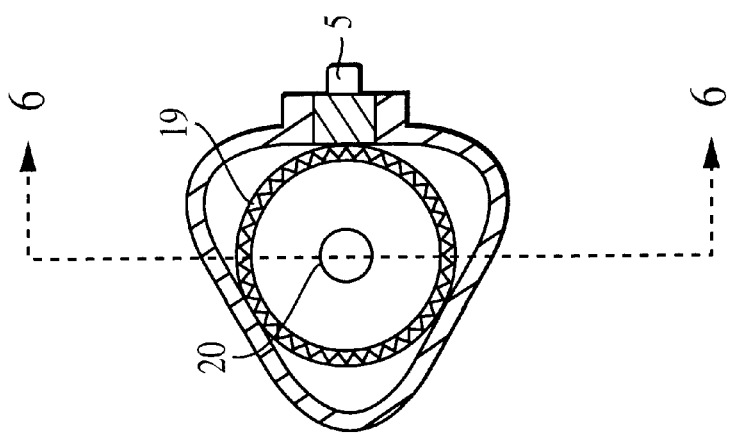
FIG. 5, shows a side view of the front cap looking from the proximal direction or from a direction where the front cap attaches to the body of the lancet device, it should be noted that the nut, stop cap, and cylindrical washer are removed.

FIG. 5 shows a view of front cap 3 of FIG. 2 looking from the direction of proximal end 39. A manual release button 5 is shown but the details of its structure and operation are not disclosed here since these aspects are discussed in detail in U.S. Pat. No. 5,797,942, incorporated by reference herein. As can be seen, front cap 3 has an internal spline 19 formed therein. Moreover, internal spline 19 is preferably formed integrally with front cap 3. Front cap also includes distal opening 20 which allows needle 7 to project therethrough.

Figure 6:
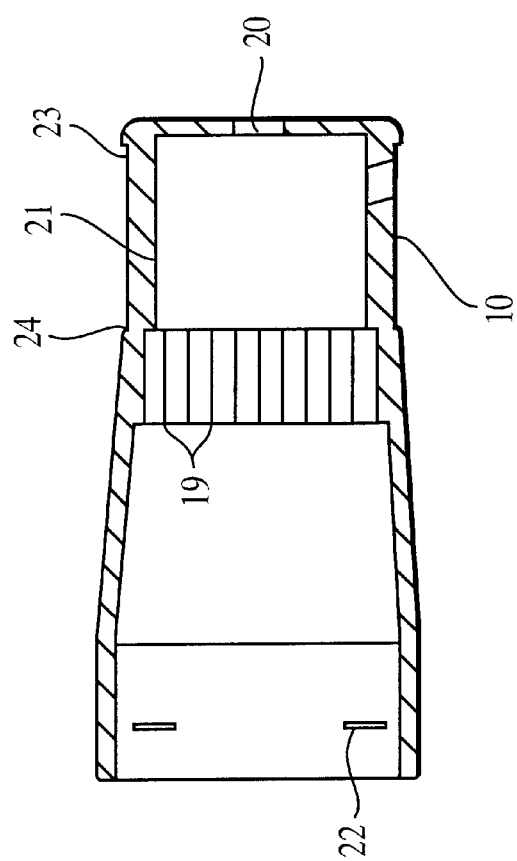
FIG. 6, shows a cross-section view along line 6—6 of FIG. 5.

As seen above and in FIG. 6, front cap 3 has bearing surface 10. Bearing surface 10 is defined by a rear retaining shoulder 24 which prevents nut 6 from moving axially in the direction of proximal end 39. Moreover, a front retaining shoulder 23 is also utilized to prevent nut 6 from moving axially in the direction of distal end 4. Bearing surface 10 is thus made with a smaller diameter than either of the cylindrical surfaces arranged adjacent retaining shoulders 23, 24. Preferably, shoulder 23 is only slightly larger than bearing surface 10 in diameter. Moreover, nut 6 has an internal diameter 39 (see FIG. 19) which is slightly smaller than front retaining shoulder diameter 23 so that nut 6 can snap onto front cap 3 and be retained axially thereby. There should also be a small clearance between nut 6 internal diameter 39 and bearing surface 10 diameter so that nut 6 can rotate freely thereon.

Figure 7:
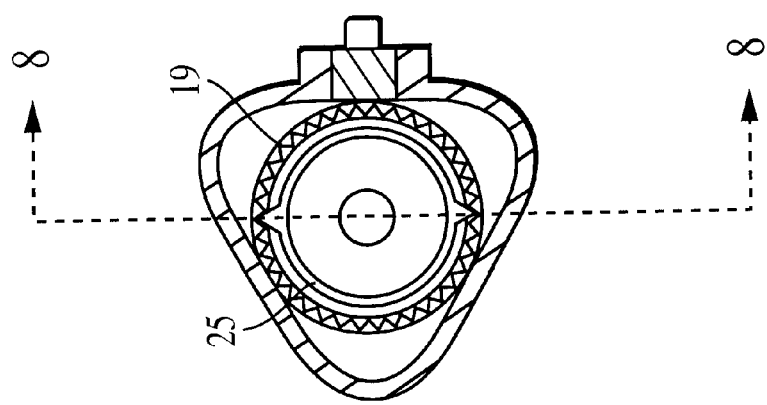
FIG. 7, shows a side view of the front cap looking from the proximal direction or from a direction where the front cap attaches to the body of the lancet device, it should be noted that this figure is similar to FIG. 5 except that the stop cap has been added.

FIG. 7 is similar to FIG. 5 but includes lancet stop element or stop cap 25 installed in front cap 3. Stop cap 25 has ratchet teeth 26 (see also FIG. 9) which engage internal spline 19 of front cap 3.

Figure 8:
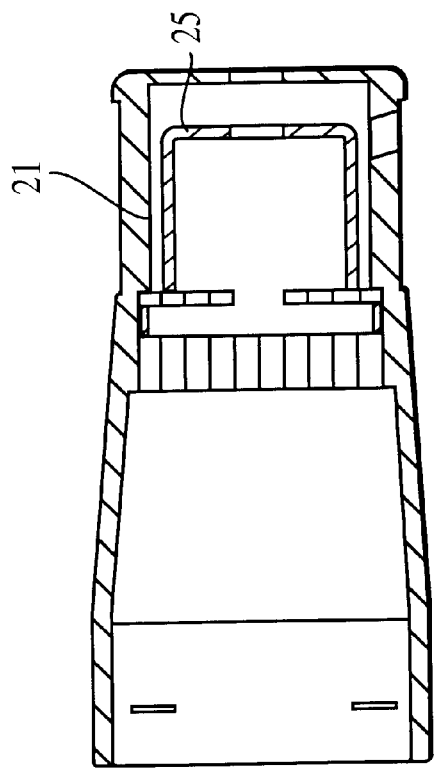
FIG. 8, shows a cross-section view along line 8—8 of FIG. 7.

FIG. 8 shows a cross-section view of front cap 3 having stop cap 25 installed therein. Stop cap 25 can move with respect to inner sliding surface 21 of front cap 3. For this purpose a clearance is shown between an outer diameter of stop cap 25 and inner sliding surface 21 of front cap 3. Moreover, each of stop cap 25 and front cap 3 have distal openings 31 and 20 respectively which should be aligned so that needle 7 can pass therethrough. The size of these openings 20, 31 is not important unless it is so large that lancet 37 (see FIG. 22) is not prevented from stopping, or so small that needle 7, cannot pass therethrough without interference.

FIG. 9 shows an enlarged view of FIG. 7. Stop cap 25 has at least one and preferably two ratchet projections or teeth 26. Ratchet teeth 26 may be integrally formed with stop cap 25. In operation, the rotation of nut 6 causes camming lug 18 to be engaged by recess 33 of nut 6 (see FIGS. 19 and 24). Camming lug 18 is also guided within camming slot 17 during its rotational movement. This design means that stop cap 25 experiences both an axial movement and a rotational movement when nut 6 is rotated. That is, stop cap 25 may rotate clockwise when it moves towards distal end 4 and counterclockwise when moving away from distal end 4 based upon corresponding rotational movements of nut 6. However, this movement is to a great extent dependent on the configuration of camming slot 17. Therefore, by changing the angle and/or shape of camming slot 17, other complex movements may also be achieved.

FIG. 9 also shows in detail how internal spline 19 is arranged to cooperate with ratchet teeth 26. The number and/or size of ratchet teeth 26 and spline teeth 19 may be designed with a fine configuration (more smaller teeth), a medium configuration (less teeth of medium size) or a large configuration (even fewer larger teeth). These configurations can be chosen, along with the number of ratchet teeth 26 so that a desired amount of torque resistance is achieved. Thus, for example, using more and smaller teeth on spline 19 would generally make it easier to rotate stop cap 25 and nut 6. Alternatively, fewer and larger spline teeth 19 would generally require more torque to rotate stop cap 25 and nut 6. Moreover, the number of ratchet teeth 26 disposed on stop cap 25 also increases the required torque to rotate stop cap 25. In the preferred device, the number of teeth of each is set so that an average user can cause rotation, and therefore adjustment, with the minimum of effort. However, providing for increased torque may be advantageous as a way to child proof the device or as a way to prevent inadvertent changes in the required depth settings. It should be noted at this point, that the invention also contemplates that front cap utilize one or two ratchet teeth while the stop cap 25 employs an external spline (not shown). The choice of which configuration to use is a matter of ease of fabrication. Additionally, as will be readily appreciated, other configurations may be readily employed other than teeth and a spline.

Figure 10:
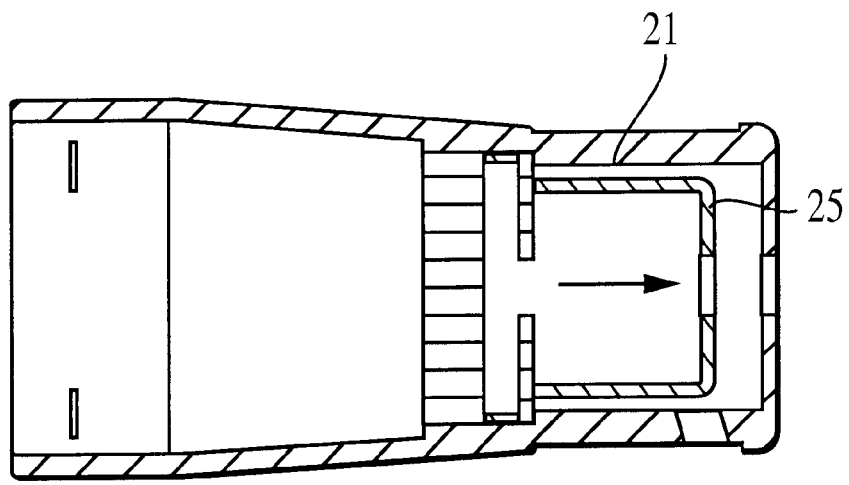
FIG. 10, shows a view similar to that of FIG. 8 and illustrates movement of the stop cap towards the distal end of the front cap, such movement indicating an adjustment towards greater needle depth penetration.

FIG. 10 shows front cap 3 with stop cap 25 disposed within in an assembled manner. The arrow indicates that stop cap 25 can move axially in the indicated direction. As a result of this movement, a greater needle depth of penetration will result.

Figure 11:
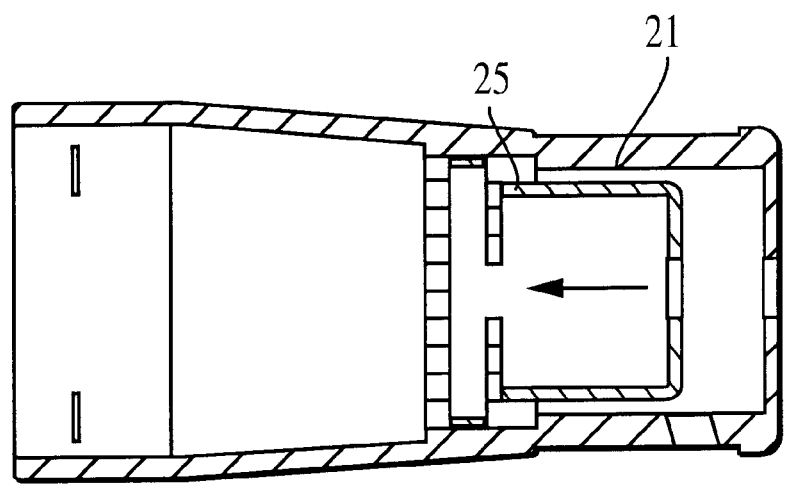
FIG. 11, shows a view similar to that of FIG. 8 and illustrates movement of the stop cap away from the distal end of the front cap, such movement indicating an adjustment towards lesser needle depth penetration.

FIG. 11 also shows front cap 3 with stop cap 25 disposed within in the assembled manner. The arrow indicates that stop cap 25 can move axially in the indicated direction. As a result of this movement, a lesser depth of needle penetration will result.

In both FIGS. 10 and 11 it is important to note that axial length of internal spline 19 should be of sufficient length so that ratchet teeth 26 always engage internal spline teeth 19, throughout the entire range of movement of stop cap 25.

Figure 12:
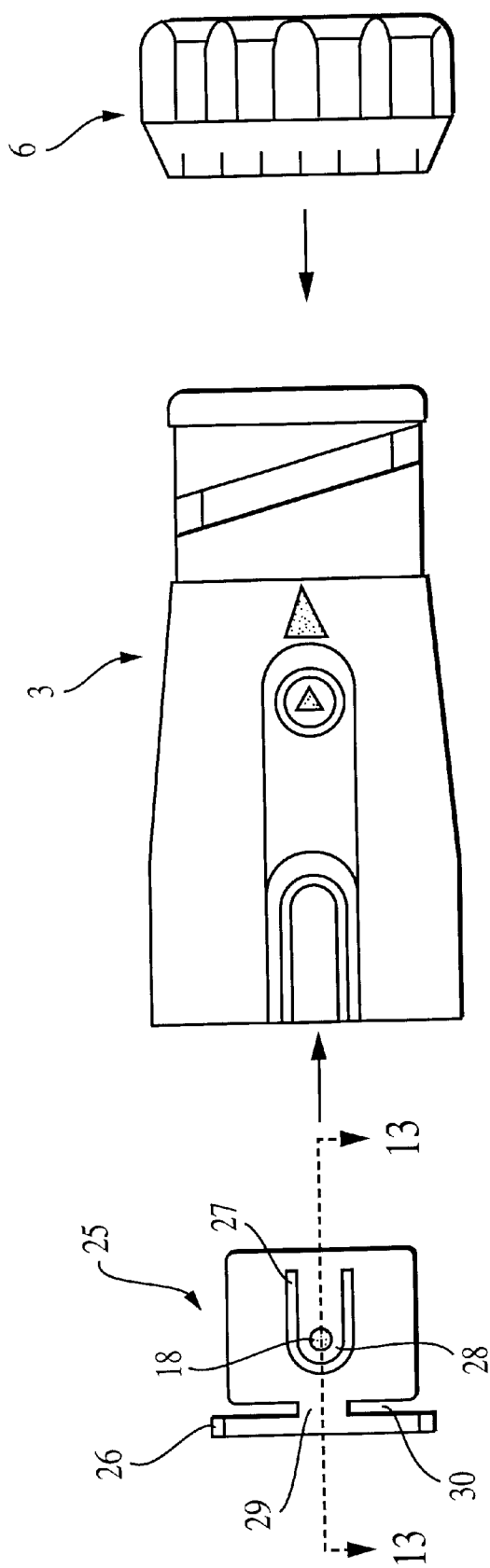
FIG. 12, shows a view similar to that of FIGS. 2 and 3 with the front cap main parts in a dis-assembled manner, the stop cap being positionable inside the front cap from the proximal end, and the nut being positionable onto the front cap from the distal end.

FIG. 12 shows front cap mechanism 3 in a dis-assembled state except that cylindrical washer or retaining sleeve 32 is removed. Stop cap 25 resembles a cap with one end open and the other end substantially closed. However, the substantially closed end is provided with an opening through which the lancet needle may project. The proximal end or first section is defined by at least one ratchet tooth and preferably two ratchet teeth 26 and a cylindrical wall on which they are formed. A separating or connecting wall 29 connects ratchet teeth 26 cylindrical wall to the remaining portion of stop cap 25. Two proximal slots 30 act to partially separate ratchet teeth 26 cylindrical wall from the remaining part of stop cap 25 and as a result allows this section to flex slightly when ratchet teeth 26 are moved and rotated with respect to internal spline 19. The width and shape of these slots 30 and connecting wall 29 can be varied depending on factors such as the material and wall thickness of stop cap 25. The remaining cap shaped portion of stop cap 25 includes a circumferential separating slot 27 which separates a deflecting wall 28 from a portion of a circumferential wall of stop cap 25. Deflecting wall 28 connects to stop cap 25 by a connecting wall so that it can flex inwardly towards a central axis (see FIG. 14). Disposed on deflecting wall 28 is a following element or camming lug 18 which projects therefrom (see FIGS. 13–15).

As indicated by the arrows in FIG. 12, stop cap 25 is assembled into front cap 3 from proximal end 39, and as discussed previously, nut 6 is assembled from distal end 4.

Figure 15:
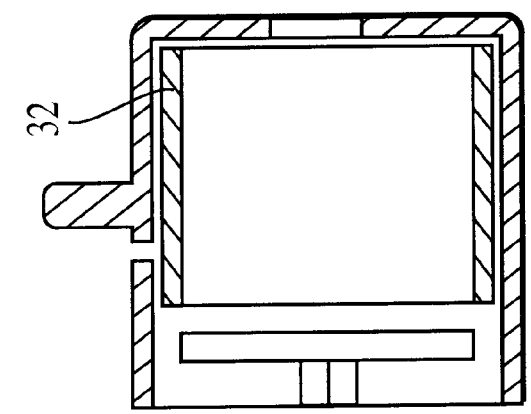
FIG. 15, shows how the cylindrical washer or retaining sleeve fits within the stop cap and illustrates how it prevents the camming lug from deflecting inward as it does in FIG. 14.
Figure 14:
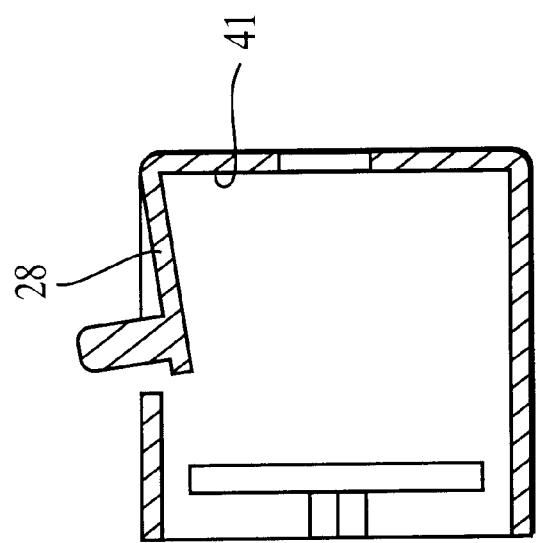
FIG. 14, shows a enlarged cross-section view of the stop cap and illustrates how the camming lug deflection wall flexes or deflects so that the stop cap may be more easily assembled into the front cap.
Figure 13:
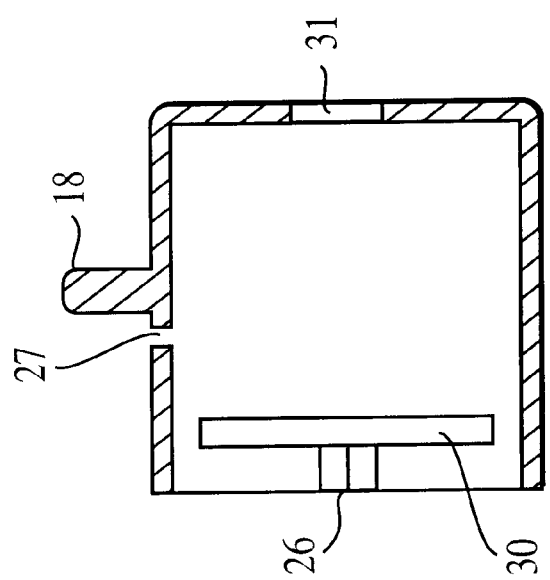
FIG. 13, shows a enlarged cross-section view of the stop cap.

FIGS. 13–15 show a cross-sectional view of stop cap 25. A distal opening 31 is disposed at distal end of stop cap 25. The cooperation of camming lug 18 and deflecting wall 28 can be seen in FIG. 14. It is important that camming lug 18 be allowed to move or deflect in this way so as to facilitate assembly of stop cap 25 into front cap 3. However, once installed, the ability of deflecting wall 28 to flex will no longer be desired (until and unless one wishes to disassemble the stop cap from the front cap). To prevent deflecting wall 28 from flexing inward at this point, or when lancet device 1 is adjusted, a retaining sleeve or cylindrical washer 32 can be disposed inside stop cap 25. As can be seen in FIG. 15, cylindrical washer 32 prevents inward flexing of deflecting wall 28. Alternatively, cylindrical washer 32 may not be required if the material of stop cap 25 is of sufficient strength or if the wall thickness of stop cap 25 is sufficiently thick to resist deflection inward when nut 6 is rotated. Preferably there is only a small clearance maintained between the outer diameter of cylindrical washer 32 and the inner diameter of stop cap 25 so that cylindrical washer 32 cannot move about or possibly back out of its position of preventing deflecting of wall 28. It is also important that the inner diameter of cylindrical washer 32 be large enough to allow lancet 37 to move within it without interference (see FIG. 22).

Figure 16:
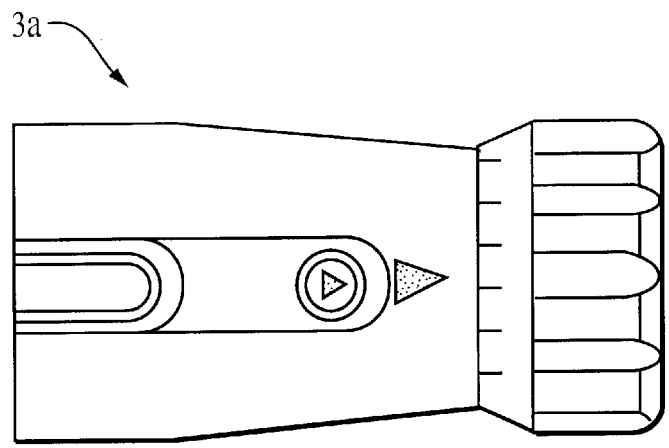
FIG. 16, shows a side view of the front cap mechanism of another embodiment, in which an extended or axially longer nut is employed.
Figure 17:
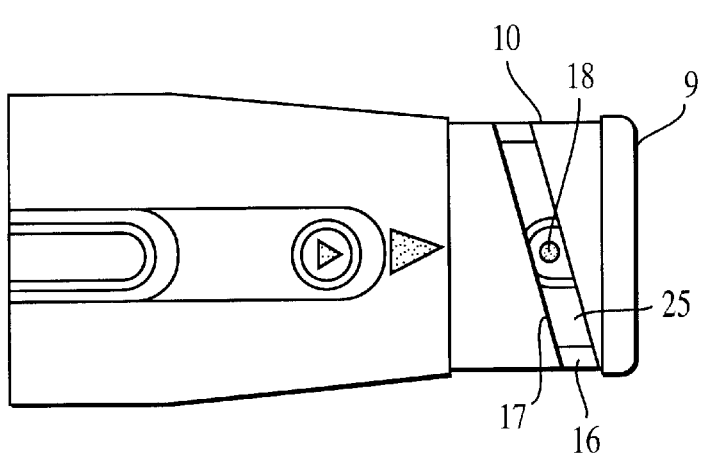
FIG. 17, shows the front cap mechanism of FIG. 16 with the nut removed therefrom.
Figure 18:
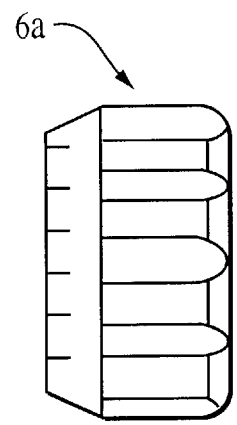
FIG. 18, shows a side view of the nut shown in FIG. 16 by itself.
Figure 21:
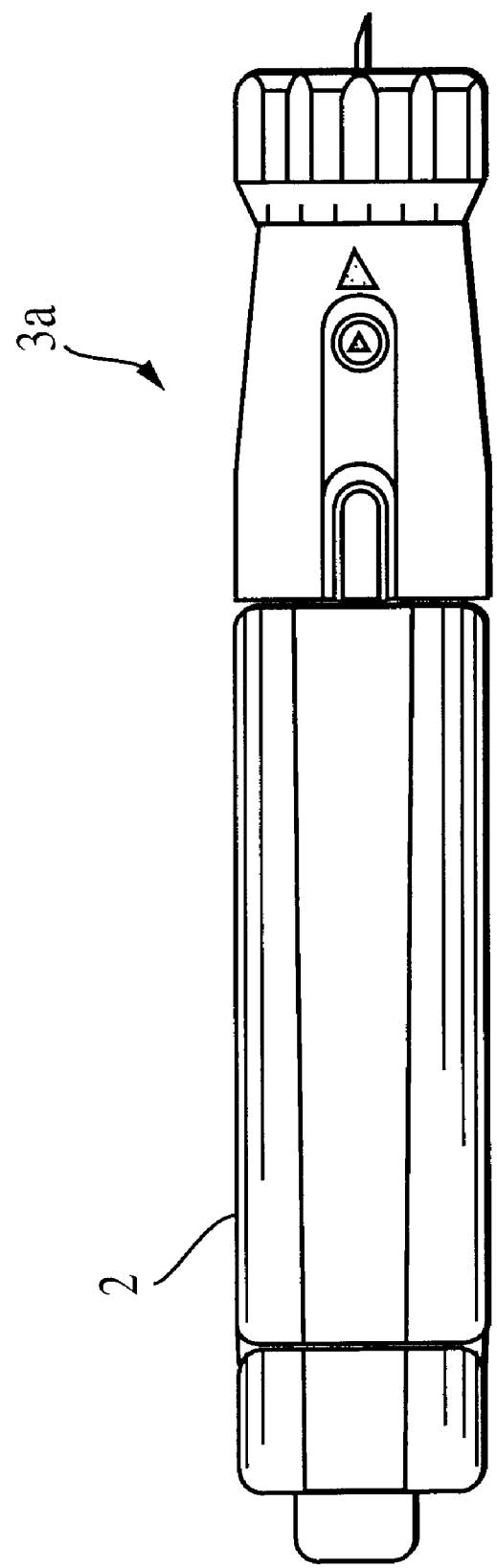
FIG. 21, shows a side view of another embodiment of the lancet device which uses the front cap of the embodiment shown in FIG. 16.

FIGS. 16–18 show an enlarged view of front cap mechanism 3a of the embodiment of FIG. 21. Front cap mechanism 3a again preferably includes manual release button 5 and reference marker arrow 13, as previously discussed with respect to the other embodiment. An extended outer sleeve or nut 6a is located on front cap 3 and is rotatable with respect to front cap 3a. Extended nut 6a also includes projections 14 and grooves 15 similar to those of nut 6. Again, as explained with respect to FIG. 4, the particular outside configuration of nut 6 less important than its ability to move and position stop cap 25.

Figure 20:
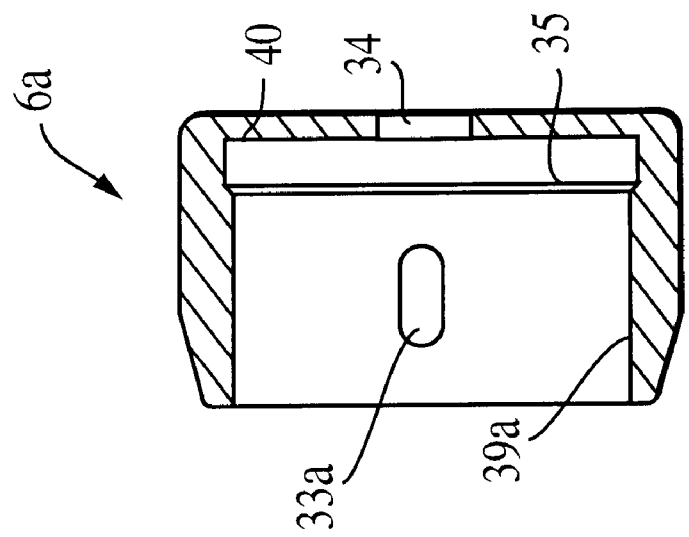
FIG. 20, shows a side cross-section view of the nut shown in FIG. 18.
Figure 19:
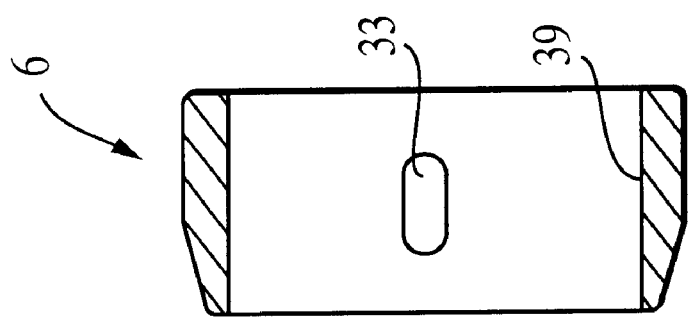
FIG. 19, shows a side cross-section view of the nut shown in FIG. 4.

As seen in FIGS. 19 and 20, extended nut 6a is similar to nut 6 except that extended nut 6a is longer axially and includes a distal wall 40 having a distal opening 34. Moreover, extended nut 6a also includes distal retaining ledge 35 which allows extended nut 6a to snap onto front cap 3a and be retained thereby. Each of nut 6 and extended nut 6a also have camming lug recess 33 and 33a. Recess 33 and 33a are in the form of a slot which is formed on the inside surface of nut 6, 6a. This recess 33, 33a, engages camming lug 18 of stop cap 25. The shape and size of recess 33, 33a can be varied so long as it functions to engage camming lug 18 throughout the range of adjustment. However, the invention contemplates that this cooperation between nut 6, 6a and stop cap 25 can be reversed. That is, nut 6, 6a could utilize a camming lug while stop cap 25 would have recess 33, 33a. However, such a design might prove to be more difficult to manufacture and, for assembly purposes, would likely require that camming lug 18 be made individually and thereafter fitted into an aperture on nut 6, 6a.

FIG. 21 shows another embodiment which uses front cap mechanism 3a and extended nut 6a, and will be described in more detail with reference to FIG. 25.

Figure 22:
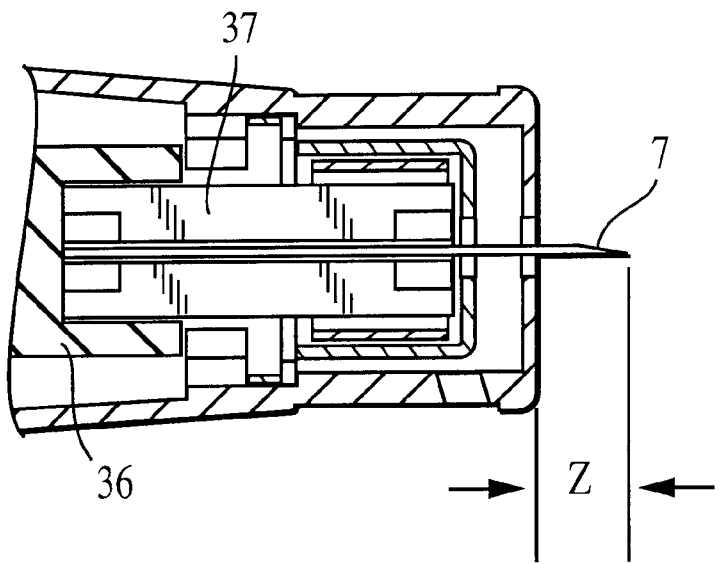
FIG. 22, shows the embodiment of FIG. 1 in partial cross-section and with the nut removed, and specifically how the lancet, internal plunger, stop cap, cylindrical washer and front cap cooperate to allow the needle to penetrate a setting depth indicated by "z"

FIG. 22 shows a partial cross-section of a condition of operation of lancet device 1 of embodiment shown in FIG. 1, with nut 6 removed. Lancet 37 contains needle 7 and is fitted onto distal end 38 of plunger 36. Stop cap 25 is set by the user by rotating nut 6 and the location of stop cap 25 prevents needle 7 from penetrating any further than a depth "z". After trigger 8 is pushed on lancet device 1, plunger 36, lancet 37, and needle 7 are caused to move towards distal end 4. Because of the position of stop cap 25, the distal end of lancet 37 contacts stop surface 50 and is thus prevented from moving any further towards distal end 4. As a result, needle 7 projects a maximum amount designated by a depth "z". It should be noted again that needle 7 is almost instantly and automatically withdrawn consistent with the operation disclosed in the Patents previously identified.

Figure 23:
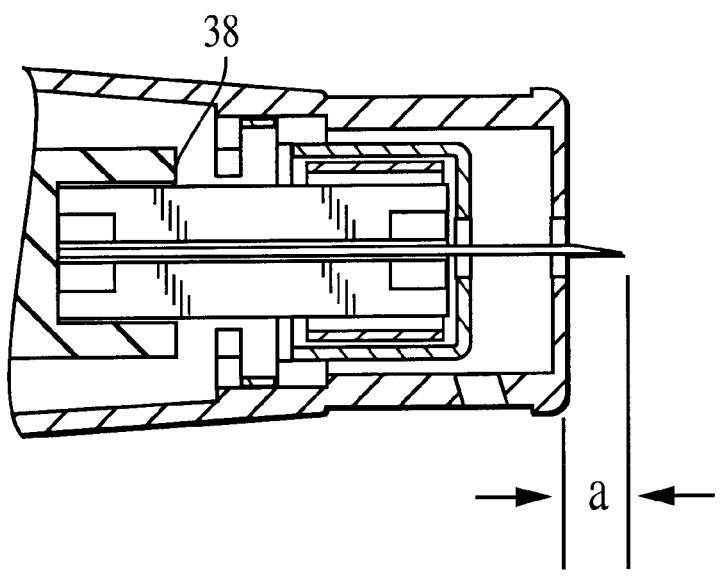
FIG. 23, shows the embodiment of FIG. 1 in partial cross-section and with the nut removed, and specifically how the lancet, internal plunger, stop cap, cylindrical washer and front cap cooperate to allow the needle to penetrate another setting depth indicated by "a"

FIG. 23 shows another setting in which stop cap 25 has moved back away from distal end 4. In this setting, stop cap 25 allows needle 7 to penetrate to a depth designated as "a". Thus, with respect to both FIGS. 22 and 23, since needle 7 is fixed to lancet 37, controlling the position of lancet 37 is tantamount to controlling the position of needle 7.

Figure 24:
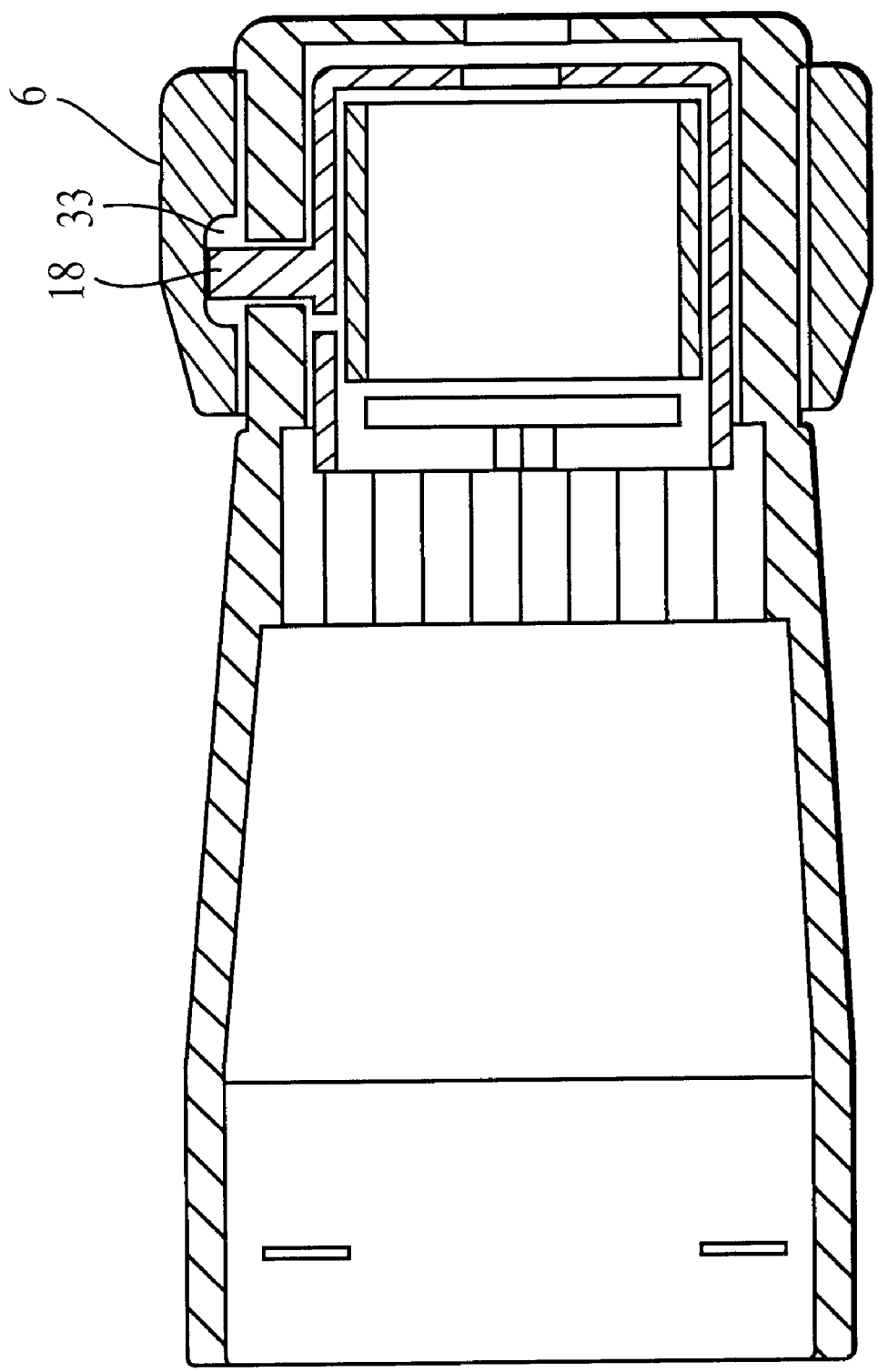
FIG. 24, shows the front cap mechanism of the embodiment of FIG. 1 in cross-section (the lancet body, lancet plunger, lancet and needle being removed), and specifically how the stop cap, cylindrical washer, nut and front cap cooperate to adjust the axial position of the stop cap within the front cap.

FIG. 24 shows front cap mechanism 3 of the embodiment of FIGS. 1–12 fully assembled. In operation, rotational movement of nut 6 causes stop cap 25 to both rotate and move axially as camming lug 18 is guided in camming slot 17. This movement sets the position of stop cap 25 within front cap 3 and defines a maximum depth of penetration of needle 7.

Figure 25:
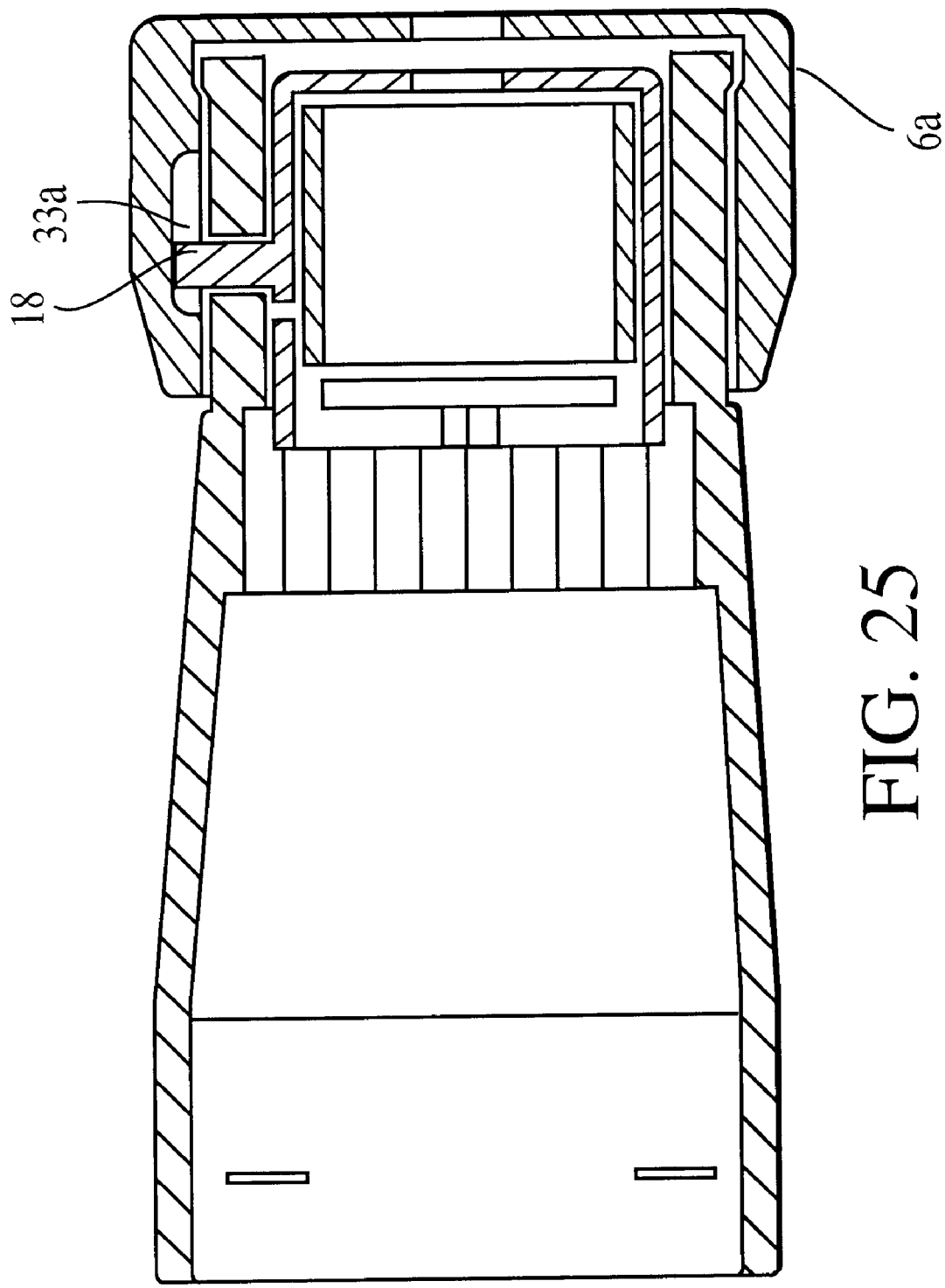
FIG. 25, shows the front cap mechanism of the embodiment of FIG. 21 in cross-section (the lancet body, lancet plunger, lancet and needle being removed), and specifically how the stop cap, cylindrical washer, nut and front cap cooperate to adjust the axial position of the stop cap within the front cap.

FIG. 25 shows front cap mechanism 3a of the embodiment of FIGS. 16–18 and 21 fully assembled. In operation, rotational movement of extended nut 6a causes stop cap 25 to both rotate and move axially as camming lug 18 is guided in camming slot 17. This movement sets the position of stop cap 25 within front cap 3a and defines a maximum depth of penetration of needle 7.

Figure 27:
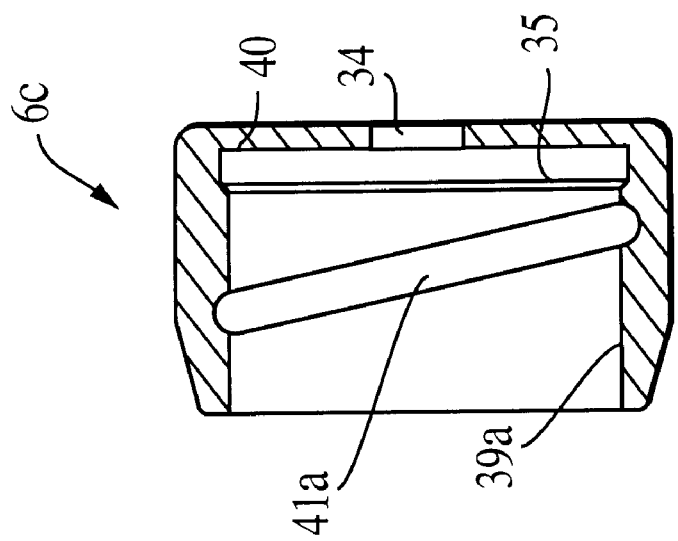
FIG. 27, shows a side cross-section view of a nut similar to that shown in FIG. 18, but of another embodiment wherein the nut itself has the camming slot instead of the front assembly which engages the camming lug of the stop cap.
Figure 26:
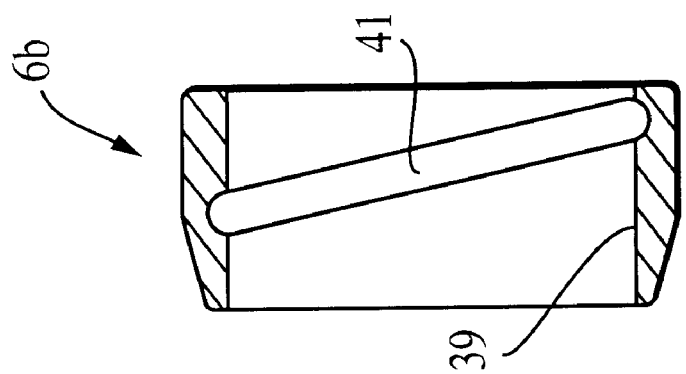
FIG. 26, shows a side cross-section view of a nut similar to that shown in FIG. 4, but of another embodiment wherein the nut itself has the camming slot instead of the front assembly which engages the camming lug of the stop cap.

As seen in FIGS. 26 and 27, nut 6b and extended nut 6c is similar to nut 6 as previously described except that it now utilizes a camming slot 41, 41a which is similar to camming slot 17. Moreover, these nut designs may be used with the embodiment shown in FIG. 32 in which the front cap camming slot 17 is replaced by a longitudinal slot 45.

Figure 29:
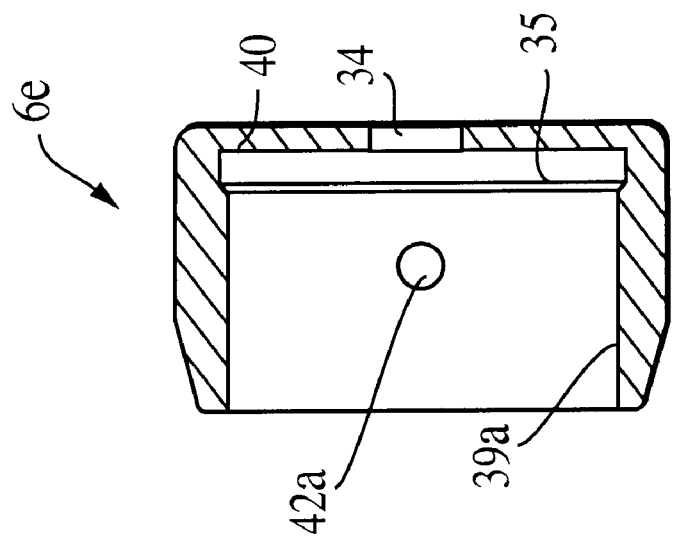
FIG. 29, shows a side cross-section view of a nut similar to that shown in FIG. 18, but of another embodiment wherein the nut itself has the camming lug instead of the stop cap.
Figure 28:
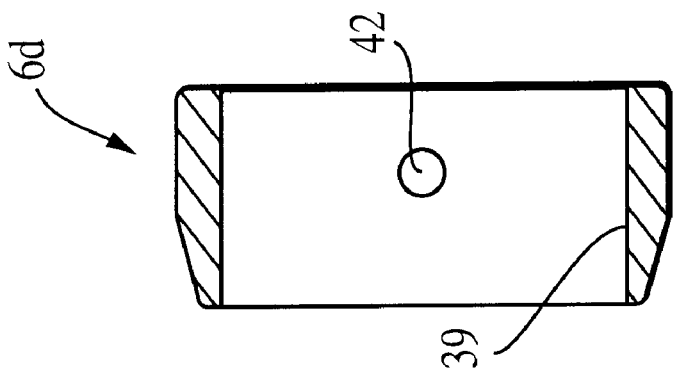
FIG. 28, shows a side cross-section view of a nut similar to that shown in FIG. 4, but of another embodiment wherein the nut itself has the camming lug instead of the stop cap.

FIGS. 28 and 29, show nut 6d and extended nut 6e which are again similar to nut 6 as previously described except that it now utilizes a following element or camming lug 42, 42a which is similar to camming lug 18. Moreover, these nut designs may be used with any of the embodiments previously described including the embodiment shown in FIG. 32 in which the front cap camming slot 17 is replaced by a longitudinal slot 45. However, this design requires that stop element or stop cap 25 be replaced by stop element or stop cap 25a (see FIG. 30).

Figure 30:
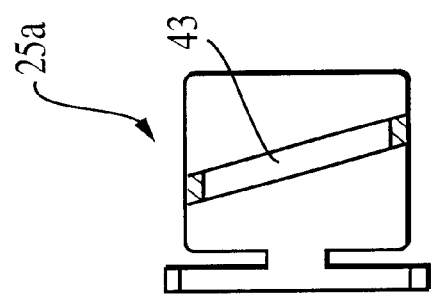
FIG. 30, shows a side view of a stop cap similar to the stop cap shown in FIG. 12, but of another embodiment wherein the stop cap has the camming slot instead of the front assembly which engages a camming lug of the nut as shown in FIGS. 28 and 29.

FIG. 30 shows stop cap 25a which differs from stop cap 25 in that the camming lug 18 is replaced by a camming slot 43. This configuration is design to work with nut 6d, 6e as shown in FIGS. 28 and 29. As can be seen from the various figures, the invention contemplates that the camming lug and camming slot configuration may take many forms. Each of the many forms has advantages and disadvantages in terms of ease of manufacturing, so the choice of which to use can be dictated by cost considerations.

Figure 31:
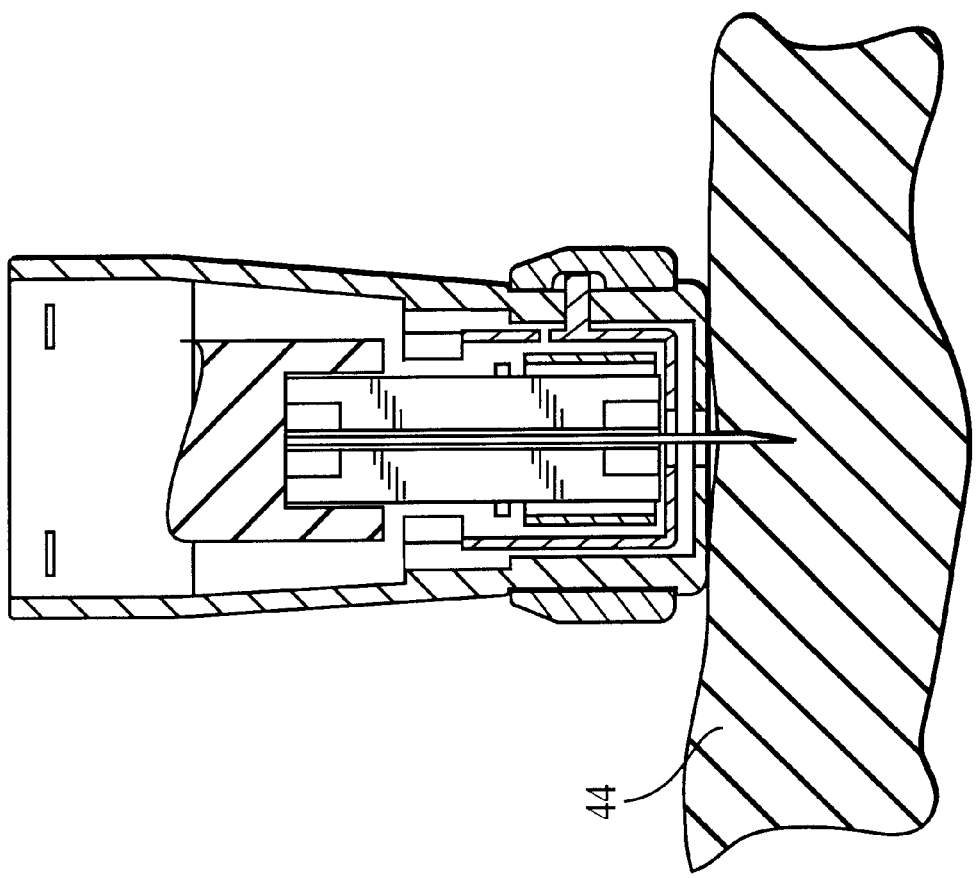
FIG. 31, shows a side cross-section view of a front assembly and lancet/needle with the needle penetrating the skin to a depth.

FIG. 31, shows a cross-section of one embodiment (FIG. 1) of the lancet device puncturing the skin 44. Thus, the rear section of the lancet device is not shown for clarity.

Figure 32:
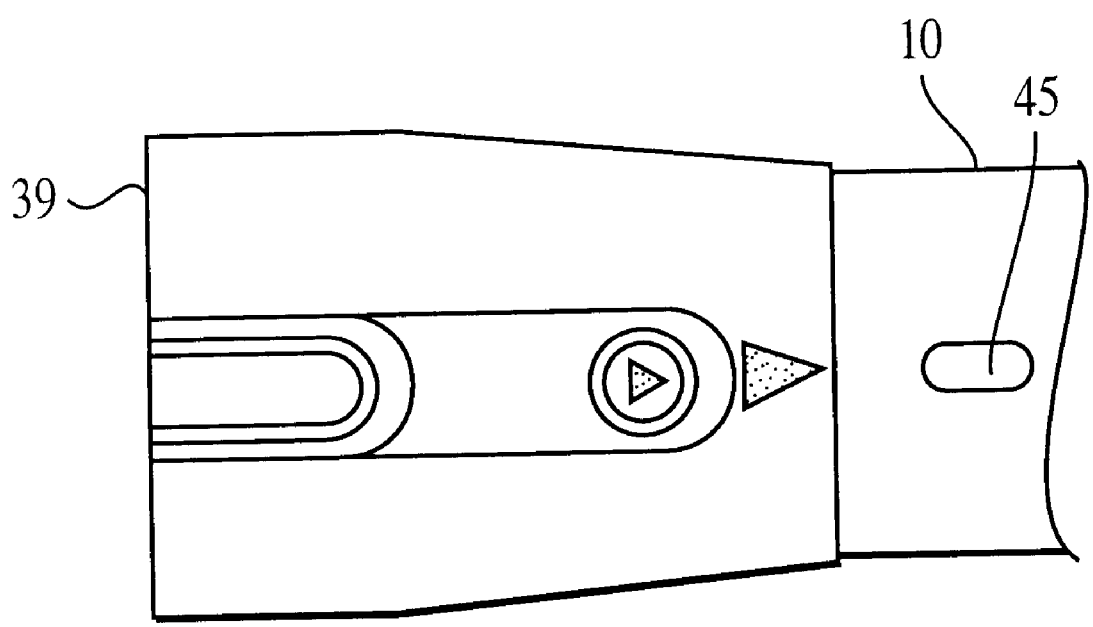

FIG. 32 shows another embodiment of the front cap in which the camming slot 17 is replaced by a longitudinal slot 45. This configuration is designed to work with stop cap 25, and nuts 6b, 6c.

One advantage of the invention is its simple design. There are few moving parts and the user can quickly learn how to use it. The device can also be manufactured relatively inexpensively since the number of parts is small, resulting is fewer assembly steps. Moreover, the parts them selves are designed to be easily fabricated. The user can learn to operate the device quickly and can realize consistent and precise results. Moreover, the device is customizable to may users and many skin thickness owing to its range of adjustability.

All the parts of the front cap mechanism may be made from plastic materials and can be formed using conventional injection molding techniques or other known manufacturing methods. The nut for example can be integrally formed with the grooves, projections, indicating marks, tapered end, and the stop cap lug slot. The stop cap may be integrally formed with its slots, ratchet projections, distal opening and camming lug. Moreover, the front cap itself may be integrally formed with the camming slot, bearing surface, front and rear retaining shoulders, internal spline, cap engaging lugs, and distal opening. Alternatively, each of these devices may be individually made as subassemblies in order to facilitate manufacture or assembly.

It should be noted that it is preferred that all the above referenced parts, except for needle 7, should ideally be made of synthetic resin or plastic material using conventional techniques such as injection molding. However, when practical, other material and manufacturing processes may also be utilized.

Figure 33:
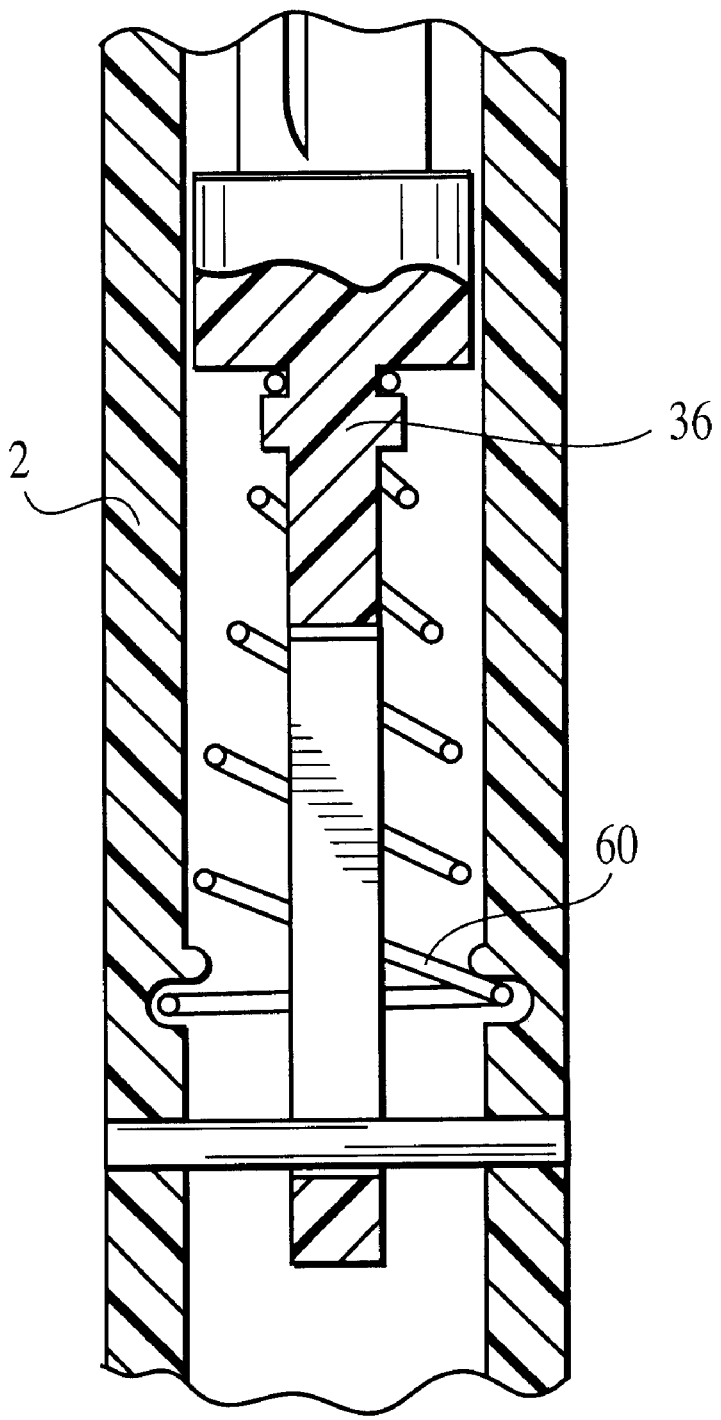
FIG. 33 is an isolated cross-sectional view illustrating a biasing element of the present invention.

In view of the above and the drawings, the lancet device 1 may comprise a housing 2 having an end; a lancet holding member 36 capable of holding a lancet 37, the lancet holding member 36 being at least partially contained within the housing 2; a biasing element 60 (see FIG. 33) capable of biasing the lancet holding member 36 toward an extended position; a trigger 8 capable of releasing the lancet holding member 36 from a retracted position; and a cap 3 capable of covering the end of the housing 2 and capable of positioning the lancet device 1 relative to a skin surface, the cap 3 comprising: a front assembly 3 comprising a side wall portion 16, a skin-engaging portion at least partially defining a plane beyond which a lancet needle 7 may extend, and a lancet stop element 25; a generally annular rotatable member 6 disposed on the front assembly 3, the generally annular rotatable member 6 comprising a slot 41a, the generally annular rotatable member 6 comprising one of a plurality of projections 14 and grooves 15 disposed on an outer surface; and at least one following element 18 extending into the slot 41a; wherein rotation of the generally annular rotatable member 6 relative to the skin engaging portion causes movement of the at least one following element 18 to move the lancet stop element 25 toward and away from the plane, to allow adjustment of a penetration depth of the lancet 37.

The lancet device tip may comprise one sleeve 6; and another sleeve 25 at least partially contained within the one sleeve 6, the another sleeve 25 comprising a stop surface 50; wherein rotation of the one sleeve 6 relative to the another sleeve 25 causes the another sleeve 25 to move at least axially without changing an overall length of the lancet device tip, as apparent from the figures, e.g., FIGS. 10 and 11.

The lancet device 1 may comprise a housing 2 having an end; a lancet holding member 36 capable of holding a lancet 37, the lancet holding member 36 being at least partially contained within the housing 2; a lancet 37 held by the lancet holding member 36; a biasing element 60 capable of biasing the lancet holding member 36 toward an extended position; a trigger 8 capable of releasing the lancet holding member 36 from a retracted position; a cap 3 capable of covering the end of the housing 2 and capable of positioning the lancet device 1 relative to a skin surface, the cap 3 comprising: a first sleeve 3; and a second sleeve 25 at least partially contained within the first sleeve 3, the second sleeve 25 comprising a stop surface 50; wherein rotation of the first sleeve 3 relative to the second sleeve 25 causes the second sleeve 25 to move at least axially without changing an overall length of the lancet device tip, as apparent from the drawings, e.g., FIGS. 10–11.

The lancet device 1 may comprise a housing 2 having an end; a lancet holding member 36 capable of holding a lancet 37, the lancet holding member 36 being at least partially contained within the housing 2; a lancet 37 held by the lancet holding member 36; a biasing element 60 capable of biasing the lancet holding member 36 toward an extended position; a trigger 8 capable of releasing the lancet holding member 36 from a retracted position; a cap 3 capable of covering the end of the housing 2 and capable of positioning the lancet device 1 relative to a skin surface, the cap 3 comprising: a first sleeve 3; a second sleeve 6 rotatably connected to the first sleeve 3 to allow relative rotation between the second sleeve 6 and the first sleeve 3; and a third sleeve, 25 contained within the first sleeve 3, the third sleeve 25 comprising a stop surface 50; wherein rotation of the second sleeve 6 relative to the first sleeve 3 causes the third sleeve 25 to move within the first sleeve 3, and wherein the lancet 37 strikes the third sleeve 25 when the lancet holding member 36 is released from the retracted position to the extended position, and wherein a penetration depth of the lancet 37 is adjustable by adjusting the position of the third sleeve 25.

Still further, the lancet device tip 3 may comprise a first sleeve 3; a second sleeve 6 rotatably connected to the first sleeve 3 to allow relative rotation between the second sleeve 6 and the first sleeve 3; and a third sleeve 25 contained within the first sleeve 3, the third sleeve 25 comprising a stop surface; and wherein rotation of the second sleeve 6 relative to the first sleeve 3 causes the third sleeve 25 to move within the first sleeve 3.

Additionally, the lancet device tip 3 may comprise a first sleeve 3; a second sleeve 6 rotatably connected to the first sleeve 3; a third sleeve 25 contained within the first sleeve 3, the third sleeve 25 comprising a stop surface; and a fourth sleeve 32 contained within the first sleeve 3 and the second sleeve 6; wherein positions of the first, second, and third sleeves are adjustable relative to each other.

The lancet device 1 may comprise a housing 2 having an end; a lancet holding member 36 capable of holding a lancet 37, the lancet holding member 36 being at least partially contained within the housing 2; a lancet 37 held by the lancet holding member 36; a biasing element 60 capable of biasing the lancet holding member 36 toward an extended position; a trigger 8 capable of releasing the lancet holding member 36 from a retracted position; a cap 3 capable of covering the end of the housing 2 and capable of positioning the lancet device 1 relative to a skin surface, the cap 3 comprising a first sleeve 3, a second sleeve 6, a third sleeve 25, and a fourth sleeve 32, wherein positions of the first, second, and third sleeves are adjustable relative to each other; and wherein the lancet strikes 37 the third sleeve 25 when the lancet holding member 36 is released from the retracted position to the extended position, and wherein a penetration depth of the lancet 37 is adjustable by adjusting the position of the third sleeve 25.

In one aspect, an overall length of the lancet device tip does not change when the second sleeve 6 is rotated relative to the first sleeve 3, as shown in the figures, e.g., FIGS. 10 and 11.

In another aspect, the second sleeve 6 comprises a slot 41a, and the third sleeve 25 comprises at least one following element 18 extending into the slot 41a.

In yet another aspect, the second sleeve 6,comprises indicia 12 that indicates a relative position of the first sleeve 3 and the third sleeve 25.

In still another aspect, the second sleeve 6 comprises a ridged surface 14 to facilitate rotation of the first sleeve 3 and the second sleeve 25 relative to each other.

In another aspect, the third sleeve 25 moves axially relative to the first sleeve 3 when the second sleeve 6 is rotated relative to the first sleeve 3.

In yet another aspect, the lancet device tip further comprises a fourth sleeve 32.

In still another aspect, the second sleeve 6 is rotatably connected between discrete predetermined positions to the first sleeve 3. The rotatable connection between discrete predetermined positions may be accomplished by at least one tooth 26, which may be in the form of a, e.g., projection and which engages spline teeth 19, which may in the form of e.g., notches.

Figure 34:
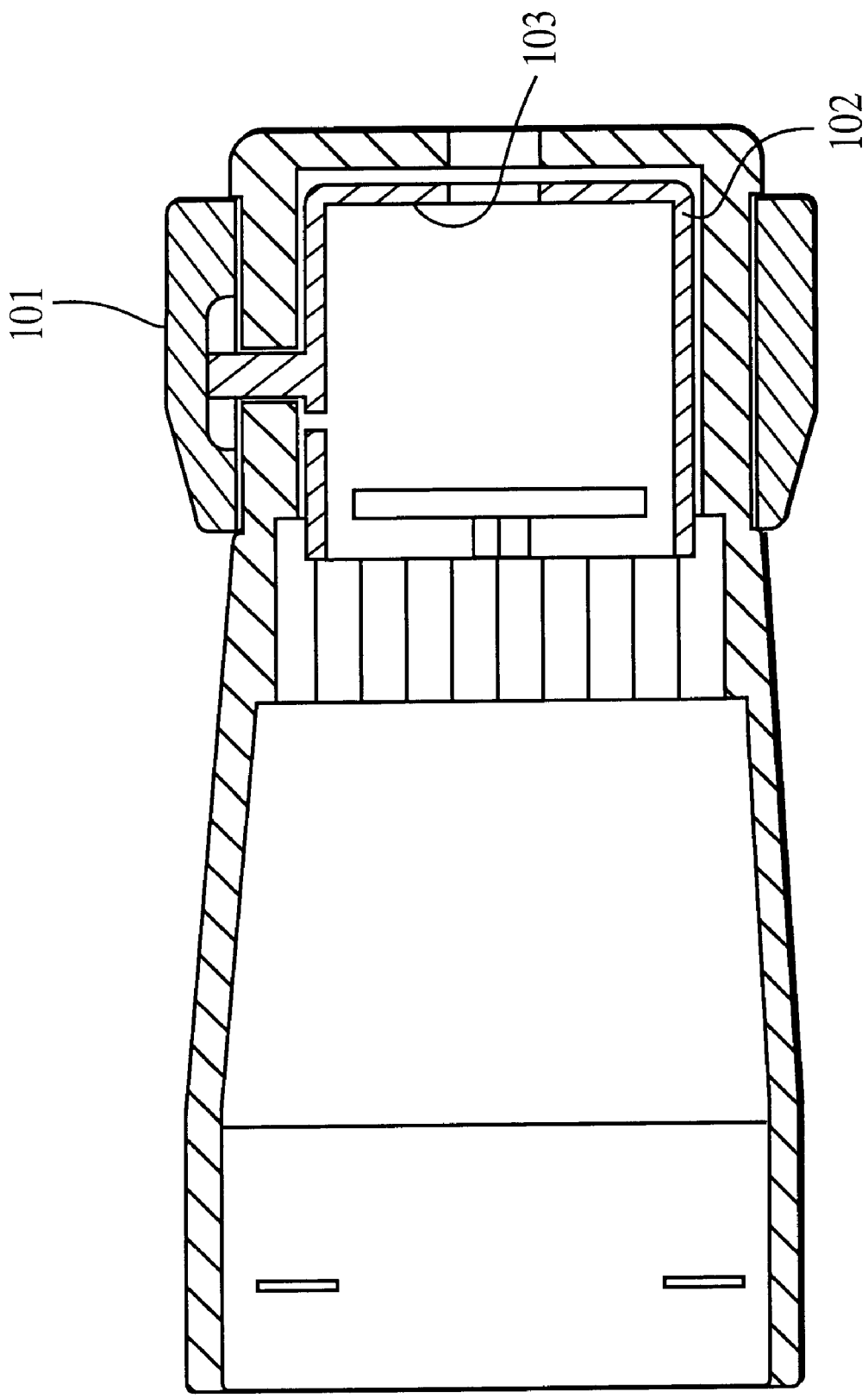
FIG. 34, shows another embodiment of a front cap mechanism in cross-section (the lancet body, lancet plunger, lancet and needle being removed), and specifically how the first sleeve and the second sleeve cooperate to adjust the axial position of the second sleeve within the first sleeve.

With reference to FIG. 34, it can be seen that another embodiment of the lancet device tip may include one sleeve 101; and another sleeve 102 at least partially contained within the one sleeve 101, the another sleeve 102 comprising a stop surface 103; wherein rotation of the one sleeve 101 relative to the another sleeve 102 causes the another sleeve 102 to move at least axially without changing an overall length of the lancet device tip.

Figure 35:
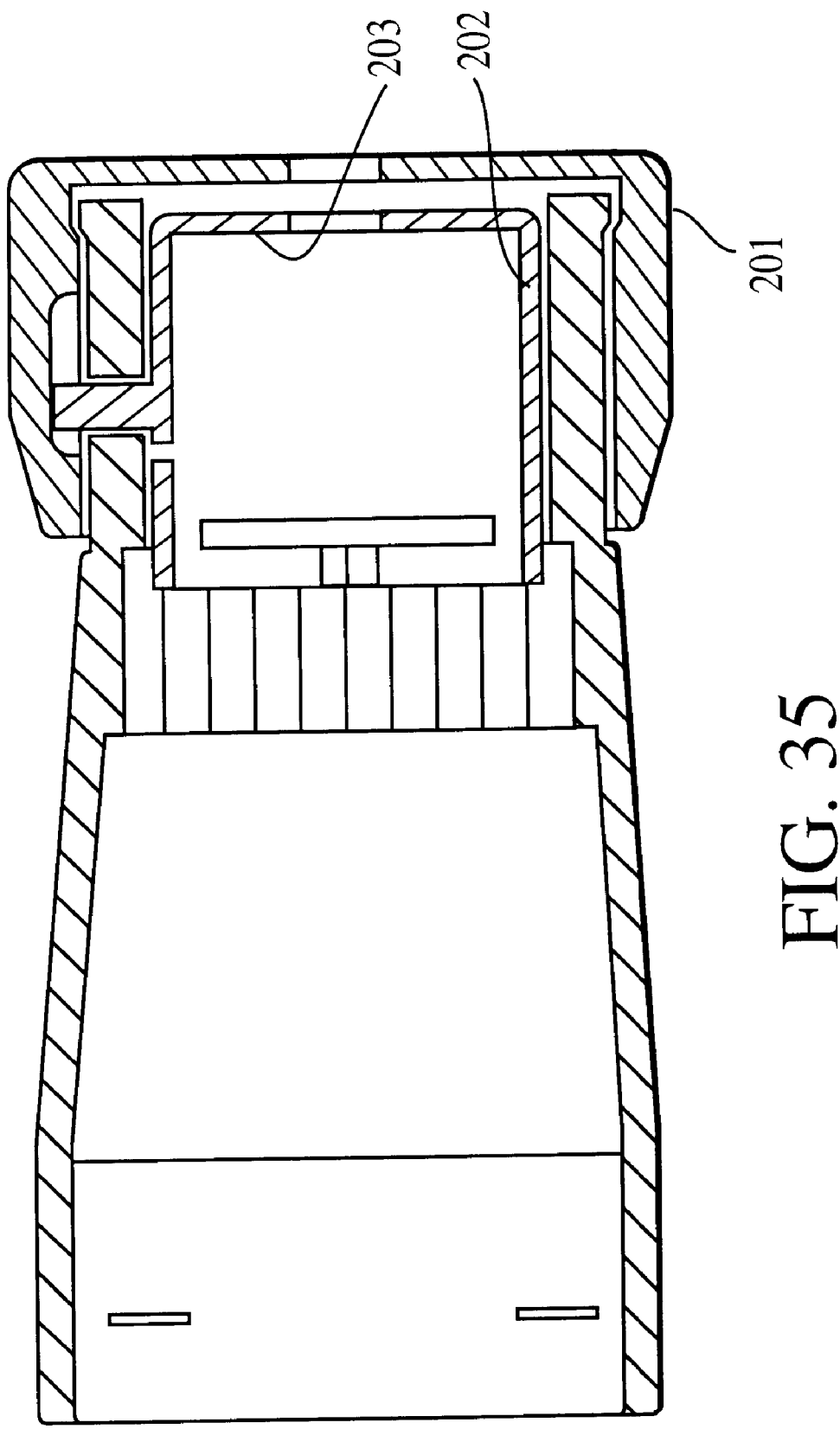
FIG. 35, shows still another embodiment of a front cap mechanism in cross-section (the lancet body, lancet plunger, lancet and needle being removed), and specifically how the first sleeve and the second sleeve cooperate to adjust the axial position of the second sleeve within the first sleeve.

With reference to FIG. 35, it can be seen that another embodiment of the lancet device tip may include one sleeve 201; and another sleeve 202 at least partially contained within the one sleeve 201, the another sleeve 202 comprising a stop surface 203; wherein rotation of the one sleeve 201 relative to the another sleeve 202 causes the another sleeve 202 to move at least axially without changing an overall length of the lancet device tip.

Figure 36:
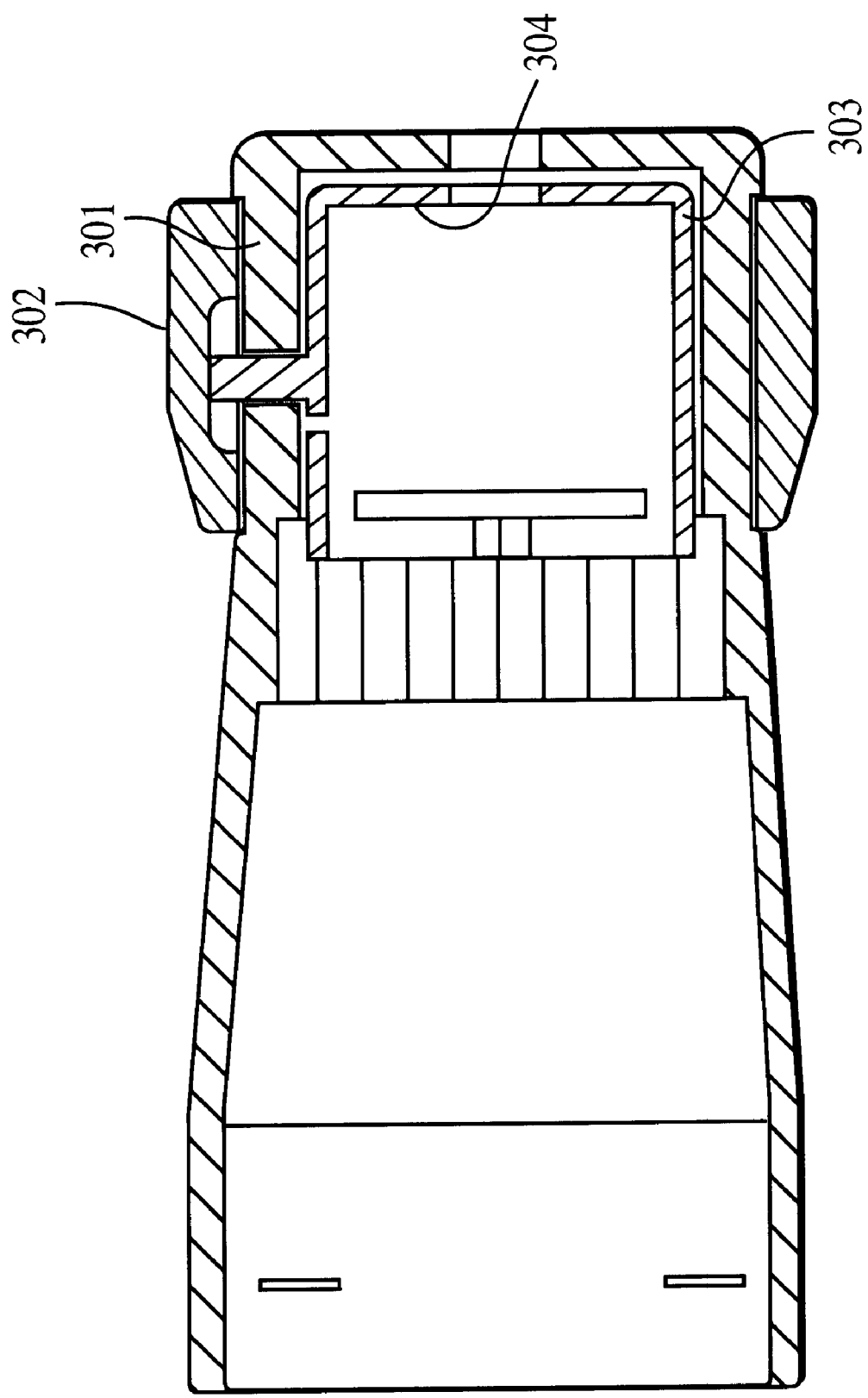
FIG. 36, shows another embodiment of a front cap mechanism in cross-section (the lancet body, lancet plunger, lancet and needle being removed), and specifically how the first sleeve, the second sleeve and the third sleeve cooperate to adjust the axial position of the third sleeve within the first sleeve.

With reference to FIG. 36, it can be seen that another embodiment of the lancet device tip may include a first sleeve 301; a second sleeve 302 rotatably connected to the first sleeve 301 to allow relative rotation between the second sleeve 302 and the first sleeve 301; and a third sleeve 303 contained within the first sleeve 301, the third sleeve 303 comprising a stop surface 304; wherein rotation of the second sleeve 302 relative to the first sleeve 301 causes the third sleeve 303 to move within the first sleeve 301, and wherein the lancet (not shown) strikes the third sleeve 303 when the lancet holding member (not shown) is released from the retracted position to the extended position, and wherein a penetration depth of the lancet is adjustable by adjusting the position of the third sleeve 303.

Figure 37:
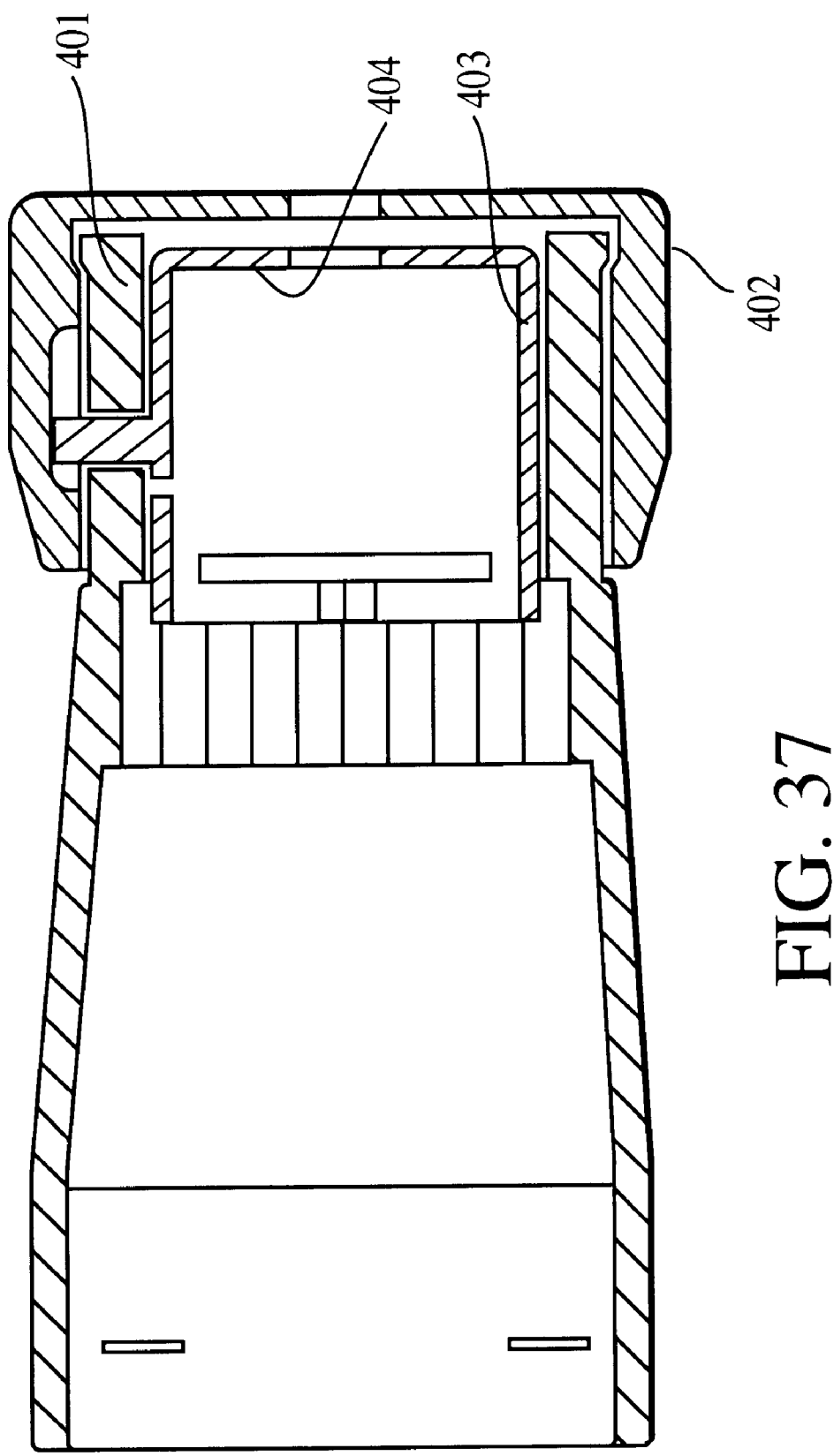
FIG. 37, shows still another embodiment of a front cap mechanism in cross-section (the lancet body, lancet plunger, lancet and needle being removed), and specifically how the first sleeve, the second sleeve and the third sleeve cooperate to adjust the axial position of the third sleeve within the first sleeve.

With reference to FIG. 37, it can be seen that another embodiment of the lancet device tip may include a first sleeve 401; a second sleeve 402 rotatably connected to the first sleeve 401 to allow relative rotation between the second sleeve 402 and the first sleeve 401; and a third sleeve 403 contained within the first sleeve 401, the third sleeve 403 comprising a stop surface 404; wherein rotation of the second sleeve 402 relative to the first sleeve 401 causes the third sleeve 403 to move within the first sleeve 401, and wherein the lancet (not shown) strikes the third sleeve 403 when the lancet holding member (not shown) is released from the retracted position to the extended position, and wherein a penetration depth of the lancet is adjustable by adjusting the position of the third sleeve 403.

Figure 38:
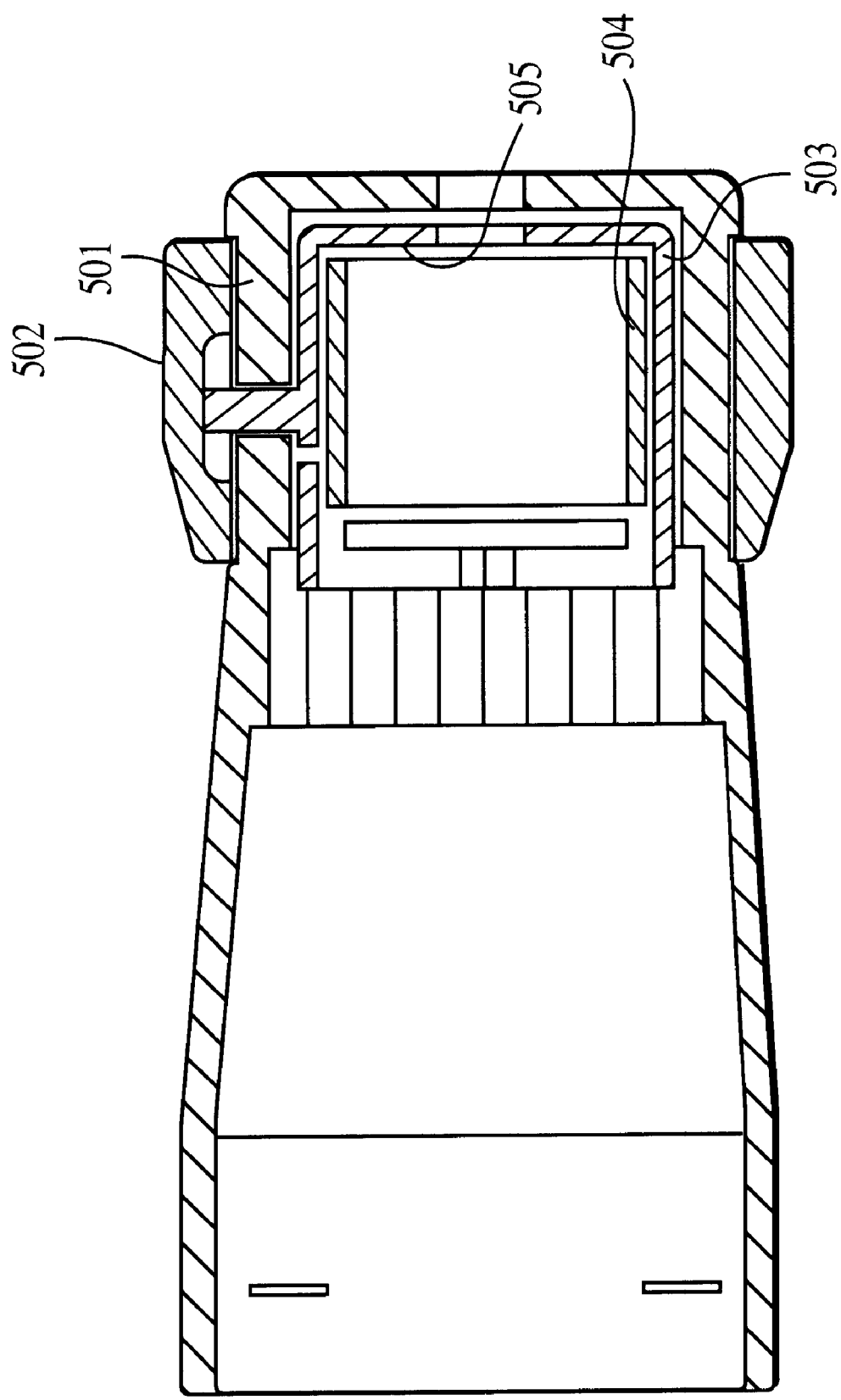
FIG. 38, shows another embodiment of a front cap mechanism in cross-section (the lancet body, lancet plunger, lancet and needle being removed), and specifically how the first sleeve, the second sleeve, the third sleeve, and the fourth sleeve cooperate to adjust the axial position of the third sleeve within the first sleeve.

With reference to FIG. 38, it can be seen that another embodiment of the lancet device tip may include a first sleeve 501; a second sleeve 502 rotatably connected to the first sleeve 501; a third sleeve 503 contained within the first sleeve 501, the third sleeve 503 comprising a stop surface 505; and a fourth sleeve 504 contained within the first sleeve 501 and the second sleeve 502; wherein positions of the first 501, second 502, and third sleeves 503 are adjustable relative to each other.

Figure 39:
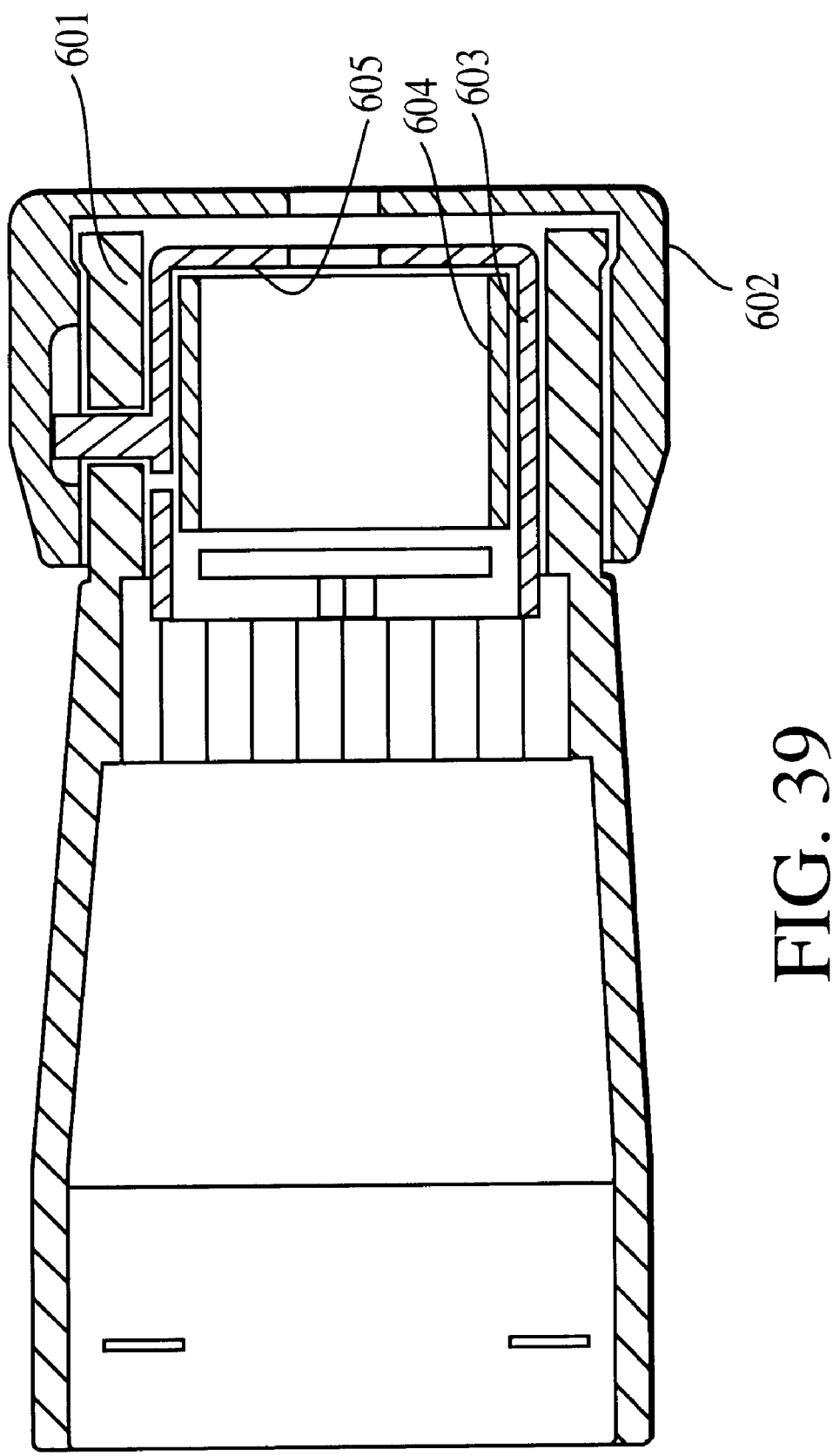
FIG. 39, shows still another embodiment of a front cap mechanism in cross-section (the lancet body, lancet plunger, lancet and needle being removed), and specifically how the first sleeve, the second sleeve, the third sleeve and fourth sleeve cooperate to adjust the axial position of the third sleeve within the first sleeve.

With reference to FIG. 39, it can be seen that another embodiment of the lancet device tip may include a first sleeve 601; a second sleeve 602 rotatably connected to the first sleeve 601; a third sleeve 603 contained within the first sleeve 601, the third sleeve 603 comprising a stop surface 605; and a fourth sleeve 604 contained within the first sleeve 601 and the second sleeve 602; wherein positions of the first 601, second 602, and third sleeves 603 are adjustable relative to each other.

It is noted that the foregoing examples have been provided merely for the purpose of explanation and are in no way to be construed as limiting of the present invention. While the present invention has been described with reference to an exemplary embodiment, it is understood that the words which have been used herein are words of description and illustration, rather than words of limitation. Changes may be made, within the purview of the appended claims, as presently stated and as amended, without departing from the scope and spirit of the present invention in its aspects. Although the present invention has been described herein with reference to particular means, materials and embodiments, the present invention is not intended to be limited to the particulars disclosed herein; rather, the present invention extends to all functionally equivalent structures, methods and uses, such as are within the scope of the appended claims.

What is claimed is:

1. A tip for a lancet device, comprising:
a front assembly comprising a side wall portion, a skin-engaging portion at least partially defining a plane beyond which a lancet needle may extend, and a lancet stop element;
a slot disposed in one of the sidewall portion and the lancet stop element;
at least one following element extending into the slot; and
an actuator comprising a generally annular rotatable member that engages the at least one following element;
wherein the lancet stop element is moveable towards and away from the plane in response to movement of the at least one following element, and
wherein the at least one following element is fixed to the lancet stop element.

2. A tip for a lancet device, comprising:
a front assembly comprising a side wall portion, a skin-engaging portion at least partially defining a plane beyond which a lancet needle may extend, and a lancet stop element;
a slot disposed in one of the sidewall portion and the lancet stop element;
at least one following element extending into the slot; and
an actuator comprising a generally annular rotatable member that engages the at least one following element;
wherein the lancet stop element is moveable towards and away from the plane in response to movement of the at least one following element, and
wherein the at least one following element is fixed to the annular member.

3. A tip for a lancet device, comprising:
a front assembly comprising a side wall portion, a skin-engaging portion at least partially defining a plane beyond which a lancet needle may extend, and a lancet stop element;
a slot disposed in one of the sidewall portion and the lancet stop element;
at least one following element extending into the slot; and
an actuator comprising a generally annular rotatable member that engages the at least one following element;
wherein the lancet stop element is moveable towards and away from the plane in response to movement of the at least one following element, and
wherein the slot is disposed on the lancet stop element.

4. The tip of claim 3, wherein the slot comprises a camming slot.

5. A tip for a lancet device, comprising:
a front assembly comprising a side wall portion, a skin-engaging portion at least partially defining a plane beyond which a lancet needle may extend, and a lancet stop element;
a slot disposed in one of the sidewall portion and the lancet stop element;
at least one following element extending into the slot;
an actuator comprising a generally annular rotatable member that engages the at least one following element; and an outer generally annular rotatable member, wherein the lancet stop element is moveable towards and away from the plane in response to movement of the at least one following element, and wherein the at least one following element is fixed to the generally annular rotatable member.

6. A tip for a lancet device, comprising:

a front assembly comprising a side wall portion, a skin-engaging portion at least partially defining a plane beyond which a lancet needle may extend, and a lancet stop element;

a slot disposed in one of the sidewall portion and the lancet stop element;

at least one following element extending into the slot;

an actuator comprising a generally annular rotatable member that engages the at least one following element; and an outer generally annular rotatable member, wherein the lancet stop element is moveable towards and away from the plane in response to movement of the at least one following element, and wherein the generally annular rotatable member comprises a slot.

7. The tip of claim 6, wherein the slot on the generally annular rotatable member comprises a camming slot.

8. A tip for a lancet device, comprising:

a front assembly comprising a side wall portion, a skin-engaging portion at least partially defining a plane beyond which a lancet needle may extend, and a lancet stop element;

a slot disposed in one of the sidewall portion and the lancet stop element;

at least one following element extending into the slot; and an actuator comprising a generally annular rotatable member that engages the at least one following element;

wherein the lancet stop element is moveable towards and away from the plane in response to movement of the at least one following element, and wherein the at least one following element is fixed to the lancet stop element.

9. A tip for a lancet device, comprising:

a front assembly comprising a side wall portion, a skin-engaging portion at least partially defining a plane beyond which a lancet needle may extend, and a lancet stop element;

a slot disposed in one of the sidewall portion and the lancet stop element;

at least one following element extending into the slot; and an actuator comprising a generally annular rotatable member that engages the at least one following element;

wherein the lancet stop element is moveable towards and away from the plane in response to movement of the at least one following element, and further comprising at least one tooth disposed on one of the lancet stop element and the front assembly.

10. The tip of claim 9, wherein the lancet stop element comprises a first section which includes at least one ratchet tooth and a second section which includes a camming lug, the first section being partially separated from the second section by at least one separating slot.

11. The tip of claim 10, wherein the first section and the second section are partially separated by at least two separating slots such that the separating slots define at least two connecting walls.

12. The tip of claim 11, wherein the second section further comprises a circumferential separating slot for separating a portion of the deflecting wall from the cylindrical wall of the lancet stop element such that the deflecting wall is connected to the cylindrical wall by a connecting wall.

13. The tip of claim 12, wherein the connecting wall allows the deflecting wall to deflect inward towards a center axis of the lancet stop element.

14. The tip of claim 11, wherein the second section further comprises a deflecting wall for connecting the camming lug to a cylindrical wall of the lancet stop element.

15. The tip of claim 9, wherein the front assembly comprises an internal spline having a plurality of teeth for engaging the at least one tooth disposed on the lancet stop element.

16. The tip of claim 9, further comprising at least two ratchet teeth being disposed on the lancet stop element approximately 180 degrees apart from one another.

17. A tip for a lancet device, comprising:

a front assembly comprising a side wall portion, a skin-engaging portion at least partially defining a plane beyond which a lancet needle may extend, and a lancet stop element;

a slot disposed in one of the sidewall portion and the lancet stop element;

at least one following element extending into the slot; and an actuator comprising a generally annular rotatable member that engages the at least one following element;

wherein the lancet stop element is moveable towards and away from the plane in response to movement of the at least one following element, and wherein the lancet stop element is moveably retained within the front assembly such that it can rotate and move axially with respect to the front assembly.

18. The tip of claim 17, wherein the lancet stop element is moveable towards and away from the plane such that at least one ratchet tooth maintains engagement with an internal spline disposed on an internal surface of the front assembly throughout this movement.

19. A tip for a lancet device, comprising:

a front assembly comprising a side wall portion, a skin-engaging portion at least partially defining a plane beyond which a lancet needle may extend, and a lancet stop element;

a slot disposed in one of the sidewall portion and the lancet stop element;

at least one following element extending into the slot; and an actuator comprising a generally annular rotatable member that engages the at least one following element;

wherein the lancet stop element is moveable towards and away from the plane in response to movement of the at least one following element, and wherein the front assembly further comprises a bearing surface disposed between at least two shoulders, and wherein an annular member is rotatably disposed on the bearing surface and is retained from axial movement by at least one shoulder.

20. A tip for a lancet device, comprising:

a front assembly comprising a side wall portion, a skin-engaging portion at least partially defining a plane beyond which a lancet needle may extend, and a lancet stop element;

a slot disposed in one of the sidewall portion and the lancet stop element;

at least one following element extending into the slot; and an actuator comprising a generally annular rotatable member that engages the at least one following element;

wherein the lancet stop element is moveable towards and away from the plane in response to movement of the at least one following element, and wherein the front assembly further comprises engaging lugs which cooperate with engaging grooves on a lancet body and a manual lancet release button for separating the lancet from the lancet body.

21. A lancet device, comprising:

a lancet body comprising a lancet firing mechanism which is at least partially enclosed within a lancet body shell;

a front assembly comprising a side wall portion, a skin-engaging portion at least partially defining a plane beyond which a lancet needle may extend, and a lancet stop element;

a slot disposed in one of the sidewall portion and the lancet stop element;

at least one following element extending into the slot; and an actuator comprising a generally annular rotatable member that engages the at least one following element;

wherein the lancet stop element is moveable towards and away from the plane in response to movement of the at least one following element.

22. A front cap mechanism for a lancet device wherein the front cap mechanism includes a proximal end for attaching to the lancet device and a distal end for allowing a needle to project therefrom, a lancet of the lancet device having a surface from which the needle projects, the mechanism comprising:

a front cap having a distal opening adapted to allow the needle to project therethrough;

a nut rotatably disposed on an outer surface of the front cap;

a stop cap movably disposed within the front cap and adapted to allow the needle to project therethrough;

the stop cap comprising a lancet stop surface and an opening;

wherein the lancet stop surface is adapted to allow the needle to project through the opening and is adapted to prevent further movement of the lancet when the surface of the lancet contacts the lancet stop surface, and wherein the stop cap further comprises at least one ratchet tooth and wherein the front cap further comprises an internal spline having a plurality of teeth for engaging the at least one ratchet tooth.

23. The mechanism of claim 22, wherein the at least one ratchet tooth comprises at least two ratchet teeth disposed approximately 180 degrees apart from one another.

24. The mechanism of claim 23, wherein the stop cap further comprises a first section which includes at least one ratchet tooth and a second section which includes a camming lug, the first section being partially separated from the section by at least one separating slot.

25. The mechanism of claim 24, wherein the second section further comprises a deflecting wall for connecting the camming lug to a cylindrical wall of the stop cap.

26. The mechanism of claim 25, wherein the second section further comprises a circumferential separating slot for separating a portion of the deflecting wall from the cylindrical wall of the stop cap such that the deflecting wall is connected to the cylindrical wall by a connecting wall.

27. The mechanism of claim 26, wherein rotation of the nut in one direction causes movement of the lancet stop surface towards the distal end and wherein rotation of the nut in the opposite direction causes movement of the lancet stop surface away from the distal end.

28. The mechanism of claim 25, wherein the camming lug is guided within the circumferential camming slot when the stop cap is moved axially or rotated and wherein the camming lug engages a recess formed on the nut.

29. The mechanism of claim 24, wherein the first section and the section are partially separated by at least two separating slots such that the separating slots define at least two connecting walls.

30. A front cap mechanism for a lancet device wherein the front cap mechanism includes a proximal end for attaching to the lancet device and a distal end for allowing a needle to project therefrom, a lancet of the lancet device having a surface from which the needle projects, the mechanism comprising:

a front cap having a distal opening adapted to allow the needle to project therethrough;

a nut rotatably disposed on an outer surface of the front cap;

a stop cap movably disposed within the front cap and adapted to allow the needle to project therethrough;

the stop cap comprising a lancet stop surface and an opening;

wherein the lancet stop surface is adapted to allow the needle to project through the opening and is adapted to prevent further movement of the lancet when the surface of the lancet contacts the lancet stop surface, and wherein the stop cap is moveably retained within the front cap such that it can rotate and move axially with respect to the front cap.

31. A tip for a lancet device, comprising:

a front assembly comprising a side wall portion, a skin-engaging portion at least partially defining a plane beyond which a lancet needle may extend, and a lancet stop element;

a slot disposed in one of the sidewall portion and the lancet stop element;

at least one following element extending into the slot; and an outer generally annular rotatable member, wherein the lancet stop element is moveable towards and away from the plane in response to movement of the at least one following element, and wherein the at least one following element is fixed to the generally annular rotatable member.

32. A tip for a lancet device, comprising:

a front assembly comprising a side wall portion, a skin-engaging portion at least partially defining a plane beyond which a lancet needle may extend, and a lancet stop element;

a slot disposed in one of the sidewall portion and the lancet stop element;

at least one following element extending into the slot; and an outer generally annular rotatable member, wherein the lancet stop element is moveable towards and away from the plane in response to movement of the at least one following element, and wherein the generally annular rotatable member comprises a slot.

33. The tip of claim 32, wherein the slot on the generally annular rotatable member comprises a camming slot.

34. A tip for a lancet device, comprising:
- a front assembly comprising a side wall portion, a skin-engaging portion at least partially defining a plane beyond which a lancet needle may extend, and a lancet stop element;
- a slot disposed in one of the sidewall portion and the lancet stop element;
- at least one following element extending into the slot; and
- the at least one following element being fixed to the lancet stop element,
- wherein the lancet stop element is moveable towards and away from the plane in response to movement of the at least one following element.

35. A tip for a lancet device, comprising:
- a front assembly comprising a side wall portion, a skin-engaging portion at least partially defining a plane beyond which a lancet needle may extend, and a lancet stop element;
- a slot disposed in one of the sidewall portion and the lancet stop element;
- at least one following element extending into the slot; and
- at least one tooth disposed on one of the lancet stop element and the front assembly,
- wherein the lancet stop element is moveable towards and away from the plane in response to movement of the at least one following element, and
- wherein the front assembly comprises an internal spline having a plurality of teeth for engaging the at least one tooth disposed on the lancet stop element.

36. A tip for a lancet device, comprising:
- a front assembly comprising a side wall portion, a skin-engaging portion at least partially defining a plane beyond which a lancet needle may extend, and a lancet stop element;
- a slot disposed in one of the sidewall portion and the lancet stop element;
- at least one following element extending into the slot; and
- at least one tooth disposed on one of the lancet stop element and the front assembly,
- wherein the lancet stop element is moveable towards and away from the plane in response to movement of the at least one following element, and
- further comprising at least two ratchet teeth being disposed on the lancet stop element approximately 180 degrees apart from one another.

37. A tip for a lancet device, comprising:
- a front assembly comprising a side wall portion, a skin-engaging portion at least partially defining a plane beyond which a lancet needle may extend, and a lancet stop element;
- a slot disposed in one of the sidewall portion and the lancet stop element;
- at least one following element extending into the slot; and
- at least one tooth disposed on one of the lancet stop element and the front assembly,
- wherein the lancet stop element is moveable towards and away from the plane in response to movement of the at least one following element, and
- wherein the lancet stop element comprises a first section which includes at least one ratchet tooth and a second section which includes a camming lug, the first section being partially separated from the second section by at least one separating slot.

38. The tip of claim 37, wherein the first section and the second section are partially separated by at least two separating slots such that the separating slots define at least two connecting walls.

39. The tip of claim 38, wherein the second section further comprises a circumferential separating slot for separating a portion of the deflecting wall from the cylindrical wall of the lancet stop element such that the deflecting wall is connected to the cylindrical wall by a connecting wall.

40. The tip of claim 39, wherein the connecting wall allows the deflecting wall to deflect inward towards a center axis of the lancet stop element.

41. The tip of claim 38, wherein the second section further comprises a deflecting wall for connecting the camming lug to a cylindrical wall of the stop cap.

42. A tip for a lancet device, comprising:
- a front assembly comprising a side wall portion, a skin-engaging portion at least partially defining a plane beyond which a lancet needle may extend, and a lancet stop element;
- a slot disposed in one of the sidewall portion and the lancet stop element;
- at least one following element extending into the slot;
- the lancet stop element being moveable towards and away from the plane in response to movement of the at least one following element;
- the lancet stop element being moveably retained within the front assembly such that it can rotate and move axially with respect to the front assembly,
- wherein the lancet stop element is moveable towards and away from the plane such that at least one ratchet tooth maintains engagement with an internal spline disposed on an internal surface of the front assembly throughout this movement.

43. A tip for a lancet device, comprising:
- a front assembly comprising a side wall portion, a skin-engaging portion at least partially defining a plane beyond which a lancet needle may extend, and a lancet stop element;
- a slot disposed in one of the sidewall portion and the lancet stop element;
- at least one following element extending into the slot; and
- the lancet stop element being moveable towards and away from the plane in response to movement of the at least one following element,
- wherein the front assembly further comprises a bearing surface disposed between at least two shoulders, and wherein an annular member is rotatably disposed on the bearing surface and is retained from axial movement by at least one shoulder.

44. A tip for a lancet device, comprising:
- a front assembly comprising a side wall portion, a skin-engaging portion at least partially defining a plane beyond which a lancet needle may extend, and a lancet stop element;
- a slot disposed in one of the sidewall portion and the lancet stop element;
- at least one following element extending into the slot; and
- the lancet stop element being moveable towards and away from the plane in response to movement of the at least one following element,
- wherein the front assembly further comprises engaging lugs which cooperate with engaging grooves on a lancet body and a manual lancet release button for separating the lancet from the lancet body.

45. A tip for a lancet device, comprising:

a front assembly comprising a side wall portion, a skin-engaging portion at least partially defining a plane beyond which a lancet needle may extend, and a lancet stop element;

a slot disposed in one of the sidewall portion and the lancet stop element;

at least one following element extending into the slot; and a rotatable nut disposed on the front assembly comprising one of a plurality of projections and grooves disposed on an outer surface, wherein the lancet stop element is moveable towards and away from the plane in response to movement of the at least one following element.

46. A lancet device comprising:

a housing having an end;

a lancet holding member capable of holding a lancet, the lancet holding member being at least partially contained within the housing;

a biasing element capable of biasing the lancet holding member toward an extended position;

a trigger capable of releasing the lancet holding member from a retracted position; and a cap capable of covering the end of the housing and capable of positioning the lancet device relative to a skin surface, the cap comprising:
  a front assembly comprising a side wall portion, a skin-engaging portion at least partially defining a plane beyond which a lancet needle may extend, and a lancet stop element;
  a generally annular rotatable member disposed on the front assembly, the generally annular rotatable member comprising a slot, the generally annular rotatable member comprising one of a plurality of projections and grooves disposed on an outer surface; and
  at least one following element extending into the slot;
wherein rotation of the generally annular rotatable member relative to the skin engaging portion causes movement of the at least one following element to move the lancet stop element toward and away from the plane, to allow adjustment of a penetration depth of a lancet.

47. A lancet device comprising:

a housing having an end;

a lancet holding member capable of holding a lancet, the lancet holding member being at least partially contained within the housing;

a lancet held by the lancet holding member;

a biasing element capable of biasing the lancet holding member toward an extended position;

a trigger capable of releasing the lancet holding member from a retracted position;

a cap capable of covering the end of the housing and capable of positioning the lancet device relative to a skin surface, the cap comprising:
  a first sleeve; and
  a second sleeve at least partially contained within the first sleeve, the second sleeve comprising a stop surface;
wherein rotation of the first sleeve relative to the second sleeve causes the second sleeve to move at least axially without changing an overall length of the lancet device tip.

48. A lancet device tip, comprising:

a first sleeve;

a second sleeve rotatably connected to the first sleeve to allow relative rotation between the second sleeve and the first sleeve; and a third sleeve contained within the first sleeve, the third sleeve comprising a stop surface; and wherein rotation of the second sleeve relative to the first sleeve causes the third sleeve to move within the first sleeve.

49. The lancet device tip of claim 48, wherein the second sleeve is rotatably connected between discrete predetermined positions to the first sleeve.

50. The lancet device tip of claim 49, wherein the rotatable connection between discrete predetermined positions comprises at least one projection which engages notches.

51. The lancet device tip of claim 48, wherein an overall length of the cap does not change when the second sleeve is rotated relative to the first sleeve.

52. The lancet device tip of claim 48, wherein the second sleeve comprises a slot, and wherein the third sleeve comprises at least one following element extending into the slot.

53. The lancet device tip of claim 48, wherein the second sleeve comprises indicia that indicates a relative position of the first and third sleeves.

54. The lancet device tip of claim 48, wherein the second sleeve comprises a ridged surface to facilitate rotation of the first and second sleeves relative to each other.

55. The lancet device tip of claim 48, wherein the third sleeve moves axially relative to the first sleeve when the second sleeve is rotated relative to the first sleeve.

56. The lancet device tip of claims 48, further comprising a fourth sleeve.

57. A lancet device comprising:

a housing having an end;

a lancet holding member capable of holding a lancet, the lancet holding member being at least partially contained within the housing;

a lancet held by the lancet holding member;

a biasing element capable of biasing the lancet holding member toward an extended position;

a trigger capable of releasing the lancet holding member from a retracted position;

a cap capable of covering the end of the housing and capable of positioning the lancet device relative to a skin surface, the cap comprising:
  a first sleeve;
  a second sleeve rotatably connected to the first sleeve to allow relative rotation between the second sleeve and the first sleeve; and
  a third sleeve contained within the first sleeve, the third sleeve comprising a stop surface;
wherein rotation of the second sleeve relative to the first sleeve causes the third sleeve to move within the first sleeve, and wherein the lancet strikes the third sleeve when the lancet holding member is released from the retracted position to the extended position, and wherein a penetration depth of the lancet is adjustable by adjusting the position of the third sleeve.

58. The lancet device of claim 57, wherein the second sleeve is rotatably connected between discrete predetermined positions to the first sleeve.

59. The lancet device of claim 58, wherein the rotatable connection between discrete predetermined positions comprises at least one projection which engages notches.

60. The lancet device of claim 57, wherein an overall length of the cap does not change when the second sleeve is rotated relative to the first sleeve.

61. The lancet device of claim 57, wherein the second sleeve comprises a slot, and wherein the third sleeve comprises at least one following element extending into the slot.

62. The lancet device of claim 57, wherein the second sleeve comprises indicia that indicates a relative position of the first and third sleeves.

63. The lancet device of claim 57, wherein the second sleeve comprises a ridged surface to facilitate rotation of the first and second sleeves relative to each other.

64. The lancet device of claim 57, wherein the third sleeve moves axially relative to the first sleeve when the second sleeve is rotated relative to the first sleeve.

65. The lancet device of claim 57, further comprising a fourth sleeve.

66. A lancet device tip, comprising:

a first sleeve;

a second sleeve rotatably connected to the first sleeve;

a third sleeve contained within the first sleeve, the third sleeve comprising a stop surface; and a fourth sleeve contained within the first and second sleeves;

wherein positions of the first, second, and third sleeves are adjustable relative to each other.

67. The lancet device tip of claim 66, wherein an overall length of the lancet device tip does not change when the positions of the first, second, and third sleeves are adjusted relative to each other.

68. The lancet device tip of claim 66, wherein the second sleeve comprises a slot, and wherein the third sleeve comprises at least one following element extending into the slot.

69. The lancet device tip of claim 66, wherein the third sleeve moves axially relative to the first sleeve when the second sleeve is rotated relative to the first sleeve.

70. The lancet device tip of claim 66, wherein the second sleeve is rotatably connected between discrete predetermined positions to the first sleeve.

71. A lancet device comprising:

a housing having an end;

a lancet holding member capable of holding a lancet, the lancet holding member being at least partially contained within the housing;

a lancet held by the lancet holding member;

a biasing element capable of biasing the lancet holding member toward an extended position;

a trigger capable of releasing the lancet holding member from a retracted position;

a cap capable of covering the end of the housing and capable of positioning the lancet device relative to a skin surface, the cap comprising a first sleeve, a second sleeve, a third sleeve, and a fourth sleeve, wherein positions of the first, second, and third sleeves are adjustable relative to each other; and wherein the lancet strikes the third sleeve when the lancet holding member is released from the retracted position to the extended position, and wherein a penetration depth of the lancet is adjustable by adjusting the position of the third sleeve.

72. The lancet device of claim 71, wherein an overall length of the cap does not change when the positions of the first, second, and third sleeves are adjusted relative to each other.

73. The lancet device of claim 71, wherein the second sleeve comprises a slot, and wherein the third sleeve comprises at least one following element extending into the slot.

74. The lancet device of claim 71, wherein the third sleeve moves axially relative to the first sleeve when the second sleeve is rotated relative to the first sleeve.

75. The lancet device of claim 71, wherein the second sleeve is rotatably connected between discrete predetermined positions to the first sleeve.

* * * * *